US011078458B2

(12) United States Patent
Fox et al.

(10) Patent No.: US 11,078,458 B2
(45) Date of Patent: Aug. 3, 2021

(54) **GENOME-WIDE RATIONALLY-DESIGNED MUTATIONS LEADING TO ENHANCED LYSINE PRODUCTION IN *E. COLI***

(71) Applicant: Inscripta, Inc., Boulder, CO (US)

(72) Inventors: Richard Fox, Boulder, CO (US); Daniel Held, Boulder, CO (US); Eric Abbate, Boulder, CO (US); Michael Clay, Boulder, CO (US); Katherine Krouse, Boulder, CO (US); Nandini Krishnamurthy, Boulder, CO (US); Krishna Yerramsetty, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 17/159,137

(22) Filed: Jan. 26, 2021

(65) Prior Publication Data

US 2021/0155894 A1    May 27, 2021

Related U.S. Application Data

(63) Continuation of application No. 16/904,827, filed on Jun. 18, 2020, now Pat. No. 10,920,189.

(60) Provisional application No. 62/865,075, filed on Jun. 21, 2019.

(51) Int. Cl.
*C12N 1/20* (2006.01)
*C07K 14/245* (2006.01)

(52) U.S. Cl.
CPC .............. *C12N 1/20* (2013.01); *C07K 14/245* (2013.01); *C12N 2510/02* (2013.01); *C12N 2511/00* (2013.01)

(58) Field of Classification Search
None
See application file for complete search history.

(56) References Cited

U.S. PATENT DOCUMENTS

| | | | |
|---|---|---|---|
| 4,833,080 A | 5/1989 | Brent et al. | |
| 4,959,317 A | 9/1990 | Sauer et al. | |
| 5,464,764 A | 11/1995 | Capecchi et al. | |
| 5,487,992 A | 1/1996 | Capecchi et al. | |
| 5,627,059 A | 5/1997 | Capecchi et al. | |
| 5,631,153 A | 5/1997 | Capecchi et al. | |
| 5,654,182 A | 8/1997 | Wahl et al. | |
| 5,677,177 A | 10/1997 | Wahl et al. | |
| 5,710,381 A | 1/1998 | Atwood et al. | |
| 5,792,943 A | 8/1998 | Craig | |
| 5,885,836 A | 3/1999 | Wahl et al. | |
| 5,888,732 A | 3/1999 | Hartley et al. | |
| 6,074,605 A | 6/2000 | Meserol et al. | |
| 6,127,141 A | 10/2000 | Kopf | |
| 6,143,527 A | 11/2000 | Pachuk et al. | |
| 6,150,148 A | 11/2000 | Nanda et al. | |
| 6,204,061 B1 | 3/2001 | Capecchi et al. | |
| 6,277,608 B1 | 8/2001 | Hartley et al. | |
| 6,391,582 B2 | 5/2002 | Ying et al. | |
| 6,482,619 B1 | 11/2002 | Rubinsky et al. | |
| 6,509,156 B1 | 1/2003 | Stewart et al. | |
| 6,654,636 B1 | 11/2003 | Dev et al. | |
| 6,689,610 B1 | 2/2004 | Capecchi et al. | |
| 6,746,441 B1 | 6/2004 | Hofmann et al. | |
| 6,774,279 B2 | 8/2004 | Dymecki | |
| 6,916,632 B2 | 7/2005 | Chesnut et al. | |
| 6,956,146 B2 | 10/2005 | Wahl et al. | |
| 7,029,916 B2 | 4/2006 | Dzekunov et al. | |
| 7,112,715 B2 | 9/2006 | Chambon et al. | |
| 7,141,425 B2 | 11/2006 | Dzekunov et al. | |
| 7,422,889 B2 | 9/2008 | Sauer et al. | |
| 8,110,122 B2 | 2/2012 | Alburty et al. | |
| 8,110,360 B2 | 2/2012 | Serber et al. | |
| 8,153,432 B2 | 4/2012 | Church et al. | |
| 8,332,160 B1 | 12/2012 | Platt et al. | |
| 8,569,041 B2 | 10/2013 | Church et al. | |
| 8,584,535 B2 | 11/2013 | Page et al. | |
| 8,584,536 B2 | 11/2013 | Page et al. | |
| 8,667,839 B2 | 3/2014 | Kimura | |
| 8,667,840 B2 | 3/2014 | Lee et al. | |
| 8,677,839 B2 | 3/2014 | Page et al. | |
| 8,677,840 B2 | 3/2014 | Page et al. | |
| 8,697,359 B1 | 4/2014 | Zhang et al. | |
| 8,726,744 B2 | 5/2014 | Alburty et al. | |
| 8,758,623 B1 | 6/2014 | Alburty et al. | |
| 8,921,332 B2 | 12/2014 | Choulika et al. | |
| 8,926,977 B2 | 1/2015 | Miller et al. | |
| 8,932,850 B2 | 1/2015 | Chang et al. | |
| 9,029,109 B2 | 5/2015 | Hur et al. | |
| D731,634 S | 6/2015 | Page et al. | |
| 9,063,136 B2 | 6/2015 | Talebpour et al. | |

(Continued)

FOREIGN PATENT DOCUMENTS

| | | |
|---|---|---|
| CN | 2397122 Y | 9/2000 |
| EP | 2135626 A1 | 12/2009 |
| EP | 2240238 | 10/2010 |
| EP | 2395087 | 12/2011 |
| EP | 3030652 | 6/2016 |
| EP | 1766004 | 8/2016 |
| EP | 3199632 | 8/2017 |
| EP | 2459696 | 11/2017 |
| WO | WO 2003/057819 | 7/2001 |
| WO | WO2002/010183 | 2/2002 |
| WO | WO 2003/087341 | 10/2003 |
| WO | WO 2009/091578 | 7/2009 |
| WO | WO 2010/079430 | 7/2010 |

(Continued)

OTHER PUBLICATIONS

International Search Report and Written Opinion for International Application No. PCT/US20/38345, dated Nov. 23, 2020, p. 143.

(Continued)

*Primary Examiner* — Nancy J Leith

(74) *Attorney, Agent, or Firm* — Sarah Brashears; Dianna L. DeVore

(57) ABSTRACT

The present disclosure relates to various different types of variants in *E. coli* coding and noncoding regions leading to enhanced lysine production for, e.g., supplements and nutraceuticals.

24 Claims, 5 Drawing Sheets

Specification includes a Sequence Listing.

(56) References Cited

U.S. PATENT DOCUMENTS

| | | |
|---|---|---|
| 9,260,505 B2 | 2/2016 | Weir et al. |
| 9,361,427 B2 | 6/2016 | Hillson |
| 9,499,855 B2 | 11/2016 | Hyde et al. |
| 9,534,989 B2 | 1/2017 | Page et al. |
| 9,546,350 B2 | 1/2017 | Dzekunov et al. |
| 9,593,359 B2 | 3/2017 | Page et al. |
| 9,738,918 B2 | 8/2017 | Alburty et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,266,851 B2 | 4/2019 | Chen |
| 2003/0059945 A1 | 3/2003 | Dzekunov et al. |
| 2003/0073238 A1 | 4/2003 | Dzekunov et al. |
| 2003/0104588 A1 | 6/2003 | Orwar et al. |
| 2004/0110253 A1 | 6/2004 | Kappler et al. |
| 2004/0115784 A1 | 6/2004 | Dzekunov et al. |
| 2004/0171156 A1 | 9/2004 | Hartley et al. |
| 2005/0064584 A1 | 3/2005 | Bargh |
| 2005/0118705 A1 | 6/2005 | Rabbitt et al. |
| 2006/0001865 A1 | 1/2006 | Bellalou et al. |
| 2006/0224192 A1 | 10/2006 | Dimmer et al. |
| 2007/0042427 A1 | 2/2007 | Gerdes et al. |
| 2007/0105206 A1 | 5/2007 | Lu et al. |
| 2007/0231873 A1 | 10/2007 | Ragsdale |
| 2007/0249036 A1 | 10/2007 | Ragsdale et al. |
| 2008/0138877 A1 | 6/2008 | Dzekunov et al. |
| 2010/0055790 A1 | 3/2010 | Simon |
| 2010/0076057 A1 | 3/2010 | Sontheimer et al. |
| 2011/0002812 A1 | 1/2011 | Asogawa et al. |
| 2011/0003303 A1 | 1/2011 | Pagano et al. |
| 2011/0009807 A1 | 1/2011 | Kjeken et al. |
| 2011/0065171 A1 | 3/2011 | Dzekunov et al. |
| 2011/0213288 A1 | 9/2011 | Choi et al. |
| 2011/0236962 A1 | 9/2011 | Loebbert et al. |
| 2012/0156786 A1 | 6/2012 | Bebee |
| 2013/0005025 A1 | 1/2013 | Church et al. |
| 2013/0196441 A1 | 8/2013 | Rubinsky et al. |
| 2014/0068797 A1 | 3/2014 | Doudna et al. |
| 2014/0121728 A1 | 5/2014 | Dhillon et al. |
| 2014/0199767 A1 | 7/2014 | Barrangou et al. |
| 2014/0273226 A1 | 9/2014 | Wu et al. |
| 2014/0350456 A1 | 11/2014 | Caccia |
| 2015/0072413 A1 | 3/2015 | Zenhausern et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0297887 A1 | 10/2015 | Dhillon et al. |
| 2016/0024529 A1 | 1/2016 | Carstens et al. |
| 2016/0053272 A1 | 2/2016 | Wurtzel et al. |
| 2016/0053304 A1 | 2/2016 | Wurtzel et al. |
| 2016/0076093 A1 | 3/2016 | Shendure et al. |
| 2016/0102322 A1 | 4/2016 | Ravinder et al. |
| 2016/0168592 A1 | 6/2016 | Church et al. |
| 2016/0272961 A1 | 9/2016 | Lee |
| 2016/0281047 A1 | 9/2016 | Chen et al. |
| 2016/0281053 A1 | 9/2016 | Sorek et al. |
| 2016/0289673 A1 | 10/2016 | Huang et al. |
| 2016/0298074 A1 | 10/2016 | Dai |
| 2016/0298134 A1 | 10/2016 | Chen et al. |
| 2016/0310943 A1 | 10/2016 | Woizenko et al. |
| 2016/0313306 A1 | 10/2016 | Ingber et al. |
| 2016/0354487 A1 | 12/2016 | Zhang et al. |
| 2016/0367991 A1 | 12/2016 | Cepheid |
| 2017/0002339 A1 | 1/2017 | Barrangou et al. |
| 2017/0022499 A1 | 1/2017 | Lu et al. |
| 2017/0029805 A1 | 2/2017 | Li et al. |
| 2017/0051310 A1 | 2/2017 | Doudna et al. |
| 2017/0073705 A1 | 3/2017 | Chen et al. |
| 2017/0218355 A1 | 3/2017 | Buie et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0283761 A1 | 10/2017 | Corso |
| 2017/0307606 A1 | 10/2017 | Hallock |
| 2017/0349874 A1 | 12/2017 | Jaques et al. |
| 2017/0369870 A1 | 12/2017 | Gill et al. |
| 2018/0023045 A1 | 1/2018 | Hallock et al. |
| 2018/0028567 A1 | 2/2018 | Li et al. |
| 2018/0051327 A1 | 2/2018 | Blainey et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0142196 A1 | 5/2018 | Coppeta et al. |
| 2018/0155665 A1 | 6/2018 | Zenhausern et al. |
| 2018/0169148 A1 | 6/2018 | Adair et al. |
| 2018/0179485 A1 | 6/2018 | Borenstein et al. |
| 2018/0200342 A1 | 7/2018 | Bikard et al. |
| 2018/0230460 A1 | 8/2018 | Gill et al. |
| 2019/0017072 A1 | 1/2019 | Ditommaso et al. |
| 2019/0169605 A1 | 6/2019 | Masquelier et al. |

FOREIGN PATENT DOCUMENTS

| | | |
|---|---|---|
| WO | WO 2011/072246 | 6/2011 |
| WO | WO2011/143124 | 11/2011 |
| WO | WO 2012/012779 A3 | 1/2012 |
| WO | WO2013/142578 | 9/2013 |
| WO | WO 2013/176772 | 11/2013 |
| WO | WO2014/018423 | 1/2014 |
| WO | WO2014/144495 | 9/2014 |
| WO | WO 2015/021270 | 2/2015 |
| WO | WO 2016/003485 | 1/2016 |
| WO | WO 2016/054939 | 4/2016 |
| WO | WO2016/110453 | 7/2016 |
| WO | WO 2016/145290 | 9/2016 |
| WO | WO2017/053902 | 3/2017 |
| WO | WO 2017/078631 | 5/2017 |
| WO | WO2017/083722 | 5/2017 |
| WO | WO2017/106414 | 6/2017 |
| WO | WO2017/161371 | 9/2017 |
| WO | WO2017/174329 | 10/2017 |
| WO | WO2017/186718 | 11/2017 |
| WO | WO2017/216392 | 12/2017 |
| WO | WO2017/223330 | 12/2017 |
| WO | WO 2018/015544 | 1/2018 |
| WO | WO2018/031950 | 2/2018 |
| WO | WO2018/071672 | 4/2018 |
| WO | WO2018/083339 | 5/2018 |
| WO | WO 2018/191715 | 10/2018 |
| WO | WO2019/006436 | 1/2019 |

OTHER PUBLICATIONS

Wang, et al., "Evolving the L-lysine high-producing strain of *Escherichia coli* using a newly developed high-throughput screening method", doi:10.1007/s10295-016-1803-1; J. Ind Microbial Biotechnol (2016) 43; 1227-1235.

Bao, et al., "Genome-scale engineering of *Saccharomyces cerevisiae* with single-nucleotide precision", Nature Biotechnology, doi:10.1038/nbt.4132, pp. 1-6 (May 7, 2018).

Dicarlo, et al., "Genome engineering in *Saccharomyces cervisiae* using CRISPR-Case systems", Nucleic Acids Research, 41(7):4336-43 (2013).

Eklund, et al., "Altered target site specificity variants of the I-Ppol His-Cys bis homing endonuclease" Nucleic Acids Research, 35(17):5839-50 (2007).

Garst, et al., "Genome-wide mapping of mutations at single-nucleotide resolution for protein, metabolic and genome engineering", Nature Biotechnology, 35(1):48-59 (2017).

Boles, et al., "Digital-to-biological converter for on-demand production of biologics", Nature Biotechnology, doi:10.1038/nbt.3859 (May 29, 2017).

Hsu, et al., "DNA targeting specificity of RNA-guided Cas9 nucleases", Nature Biotechnology, 31(9):827-32 (2013).

(56) References Cited

OTHER PUBLICATIONS

Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Pines, et al., "Codon Compression Algorithms for Saturation Mutagenesis", ACS Synthetic Biology, 4:604-14 (2015).
Verwaal, et al., "CRISPR/Cpf1 enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Cramer et al., "Functional association between promoter structure and transcript alternative splicing," PNAS USA, 94(21):11456-60 (1997).
Dalphin et al., "Transterm: A Database of Translational Signals," Nucl. Acids Res., 24(1): 216-218 (1996).
Datsenko and Wanner, "One-step inactivation of chromosomal genes in *Escherichia coli* K-12 using PCR products", PNAS USA, 97(12):6640-5 (2000).
De Kok et al., "Rapid and reliable DNA assembly via ligase cycling reaction," ACS Synth Biol., 3(2):97-106 (2014).
Desmet et al., "Human Splicing Finder: an online bioinformatics tool to predict splicing signals," Nucleic Acids Res., 37(9):e67 (2009).
Divina et al., "Ab Initio prediction of mutation-induced cryptic splice-site activation and exon skipping," European Journal of Human Genetics, 17:759-765 (2009).
Dong, "Establishment of a highly efficient virus-inducible CRISPR/Cas9 system in insect cells," Antiviral Res., 130:50-7(2016).
Durai et al., "Zinc finger nucleases: custom-designed molecular scissors for genome engineering of plant and mammalian cells", Nucleic Acids Res., 33(18):5978-90 (2005).
Engler et al., "PLoS One, A One Pot, One Step, Precision Cloning Method with High Throughput Capability," 3(11):e3647 (2008).
Epinat et al., "A novel engineered meganuclease induces homologous recombination in eukaryotic cells, e.g., yeast and mammalian cells", Nucleic Acids Research, 31(11): 2952-2962, 2003.
Faber et al., "Genome-wide prediction of splice-modifying SNPs in human genes using a new analysis pipeline called AASsites," BMC Bioinformatics, 12(suppl 4):S2 (2011).
Farasat et al., "A Biophysical Model of CRISPR/Cas9 Activity for Rational Design of Genome Editing and Gene Regulation," PLoS Comput Biol., 29:12(1):e1004724 (2016).
Adamo, et al., "Flow-through comb electroporation device for delivery of macromolecules", Analytical Chemistry, 85(3):1637-41 (2015).
Greger et al., "Balancing transcriptional interference and initiation on the GAL7 promoter of *Saccharomyces cerevisiae*," PNAS, 97(15):8415-20 (2000).
Juan et al., "Histone deacetylases specifically down-regulate p53-dependent gene activation," Journal of Biological Chemistry 275.27 (2000): 20436-20443.

Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1): 81-9 (2009).
Lefevre et al., "Alanine-stretch scanning mutagenesis: a simple and efficient method to probe protein structure and function, "Nucleic Acids Research, vol. 25(2):447-448 (1997).
Liu et al., "A chemical-inducible CRISPR-Cas9 system for rapid control of genome editing", Nature Chemical Biology, 12:980-987(2016).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Mullick et al., "The cumate gene-switch: a system for regulated expression in mammalian cells", BMC Biotechnology, 6:43 (2006).
Nalla et al., "Automated splicing mutation analysis by information theory," Hum. Mutat., 25:334-342 (2005).
No et al., "Ecdysone-inducible gene expression in mammalian cells and transgenic mice," PNAS, 93(8):3346-3351 (1996).
Ohtsuka, "Lantibiotics: mode of action, biosynthesis and bioengineering," Curr Pharm Biotechnol, 10(2):244-51 (2009).
Patron, "DNA assembly for plant biology: techniques and tools," Curr Opinion Plant Biol., 19:14-9 (2014).
Sands et al., "Overview of Post Cohen-Boyer Methods for Single Segment Cloning and for Multisegment DNA Assembly," Curr Protoc Mol Biol., 113:3.26.1-3.26.20 (2016).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
West et al., "Molecular Dissection of Mammalian RNA Polymerase II Transcriptional Termination," Mol Cell. 29(5):600-10 (2008).
West et al., "Transcriptional Termination Enhances Protein Expression in Human Cells," Mol Cell.; 33(3-9); 354-364 (2009).
Yoshioka, et al., "Development for a mono-promoter-driven CRISPR/CAS9 system in mammalian cells", Scientific Reports, Jul. 3, 2015, p. 1-8.
Remaut, et al., "Plasmid vectors for high-efficiency expression controlled by the PL promoter of coliphage lambda", Laboratory of Molecular Biology, Apr. 15, 1981, p. 81-93.
International Search Report and Written Opinion for International Application No. PCT/US19/46515, dated Oct. 28, 2019, p. 1-11.
International Search Report and Written Opinion for International Application No. PCT/US19/49735, dated Nov. 18, 2019, p. 1-13.
International Search Report and Written Opinion for International Application No. PCT/US19/46526, dated Dec. 18, 2019, p. 1-17.
International Search Report and Written Opinion for International Application No. PCT/US18/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US20/24341, dated Jun. 19, 2020, p. 1-9.
International Search Report and Written Opinion for International Application No. PCT/US19/47135, dated Jun. 11, 2020, p. 1-15.
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).

(56) References Cited

OTHER PUBLICATIONS

International Search Report and Written Opinion for International Application No. PCT/US2018/040519, dated Sep. 26, 2018, p. 1-8.
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Nov. 23, 2018, p. 1-12.
International Search Report and Written Opinion for International Application No. PCT/US2019/023342 dated Jun. 6, 2019, p. 1-12.
International Search Report and Written Opinion for International Application No. PCT/US2019/026836 dated Jul. 2, 2019, p. 1-10.
International Search Report and Written Opinion for International Application No. PCT/US2019/028821 dated Aug. 2, 2019, p. 1-14.
International Search Report and Written Opinion for Interational Application No. PCT/US2019/028883 dated Aug. 16, 2019, p. 1-12.
International Search Report and Written Opinion for International Application No. PCT/US2019/030085 dated Jul. 23, 2019, p. 1-14.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication for U.S. Appl. No. 16/024,831, dated Feb. 12, 2019, p. 1-37.
First Office Action Interview Pilot Program Pre-Interview Communication for U.S. Appl. No. 16/360,404 dated Jul. 1, 2019, p. 1-27.
First Office Action Interview Pilot Program Pre-Interview Communication for U.S. Appl. No. 16/360,423 dated Jul. 1, 2019, p. 1-27.
Non Final Office Action for U.S. Appl. No. 16/399,988 dated Jul. 31, 2019, p. 1-20.
First Office Action Interview Pilot Program Pre-Interview Communication for U.S. Appl. No. 16/454,865 dated Aug. 16, 2019, p. 1-36.

200,000 TOTAL EDITS

| BIOLOGICAL TARGETS | EDIT OUTCOME | EDIT TYPE | SCALE |
|---|---|---|---|
| PATHWAY ENZYMES | SITE SATURATION MUTAGENESIS -- GLOBAL | SWAP | 19 ENZYMES IN LYSINE BIOSYNTHESIS PATHWAY |
| PATHWAY ENZYMES | SITE SATURATION MUTAGENESIS -- LOCAL (FUNCTIONAL SITES) | SWAP | 19 ENZYMES IN LYSINE BIOSYNTHESIS PATHWAY |
| TRANSCRIPTION FACTORS | SITE SATURATION MUTAGENESIS -- LOCAL (DNA BINDING SITES) | SWAP | 20 TRANSCRIPTION FACTORS |
| TRUNCATED PROTEINS | PREMATURE STOPS ACROSS ALL PROTEINS | SWAP | GENOME - WIDE |
| REGULATORY ELEMENTS | TRANSCRIPTION FACTOR BINDING SITES | SWAP | TFBS UPSTREAM OF 20 ORFs |
| REGULATORY ELEMENTS | GAIN OF FUNCTION EXPRESSION MODULATION BY PROMOTER LADDERING | INSERT | GENOME - WIDE |
| REGULATORY ELEMENTS | EXPRESSION MODULATION THROUGH RIBOSOMAL BINDING SITES | INSERT | GENOME - WIDE |

FIG. 2

SEQUENCE LISTING

```
<160> NUMBER OF SEQ ID NOS: 42

<210> SEQ ID NO 1
<211> LENGTH: 292
<212> TYPE: PRT
<213> ORGANISM: Escherichia coli

<400> SEQUENCE: 1

Met Phe Thr Gly Ser Ile Val Ala Ile Val Thr Pro Met Asp Glu Lys
1               5                   10                  15

Gly Asn Val Cys Arg Ala Ser Leu Lys Lys Leu Ile Asp Tyr His Val
                20                  25                  30

Ala Ser Gly Thr Ser Ala Ile Val Ser Val Gly Thr Thr Gly Glu Ser
            35                  40                  45

Ala Thr Leu Asn His Asp Glu His Ala Asp Val Val Met Met Thr Leu
        50                  55                  60

Asp Leu Ala Asp Gly Arg Ile Pro Val Ile Ala Gly Thr Gly Ala Asn
65                  70                  75                  80

Ala Thr Ala Thr Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Ala Asn
        195                 200                 205

Val Ala Ala Arg Asp Met Ala Gln Met Cys Lys Leu Ala Ala Glu Gly
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
```

```
              275                 280                 285

Ala Gly Leu Leu
    290

<210> SEQ ID NO 2
<211> LENGTH: 121
<212> TYPE: DNA
<213> ORGANISM: Escherichia coli

<400> SEQUENCE: 2
ttgcttttaa tgccatacca aacgtaccat tgagacactt gtttgcacag aggatggccc     60
ttgacggcta gctcagtcct aggtacagtg ctagctaagt aggtacgtaa ggaggtgata    120
a                                                                     121

<210> SEQ ID NO 3
<211> LENGTH: 449
<212> TYPE: PRT
<213> ORGANISM: Escherichia coli

<400> SEQUENCE: 3
```

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu

```
            275                 280                 285
Val Cys Asn Lys Thr Glu Asn Pro Pro Leu Phe Arg Ala Leu Ala Leu
            290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Pro Asp Leu Ile Thr Ser Glu Val Ser Val Ala Leu Thr
                340                 345                 350

Leu Asp Thr Thr Gly Ser Thr Ser Thr Gly Asp Thr Leu Leu Thr Gln
                355                 360                 365

Ser Leu Leu Met Glu Leu Ser Ala Leu Cys Arg Val Glu Val Glu Glu
370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
                420                 425                 430

Gly Glu Asp Ala Glu Gln Val Val Gln Lys Leu His Ser Asn Leu Phe
                435                 440                 445

Glu

<210> SEQ ID NO 4
<211> LENGTH: 1693
<212> TYPE: DNA
<213> ORGANISM: Escherichia coli

<400> SEQUENCE: 4 ttattttaa atgagaccag gtcctcattt taataacccc tggctggaga atattgcaca    60
tttacagcta gctcagtcct aggtattatg ctagctaagt aggtacgtaa ggaggtgata   120
aatggccaac atcgaaatca gacaagaaac gccaactgcg ttttatataa agttcacga   180
cacagataat gtggcaatta ttgttaatga taatggcctg aaagcaggaa cgcgttttcc   240
ggatgggctg aattaattg aacatattcc ccaggggcat aaagtcgcat tgctggacat   300
tccggctaat ggtgaaatta ttcgttatgg cgaagtgatt ggttacgccg tgcgtgcaat   360
cccacgcgga agctggatcg acgaatcaat ggttgtacta ccggaagcgc cgccgttaca   420
cacgctgcca ctggcaacca aagtcccgga acccttaccg ccgctggaag gatacacctt   480
tgagggctat cgcaatgccg atggcagcgt gggcaccaaa aacctgctcg gtatcaccac   540
cagcgtccac tgtgtggcag gcgtggtgga ctatgtagta aaaatcattg aacgcgatct   600
gctaccgaaa tacccgaacg tcgatggcgt ggtgggctg aatcatttgt acggttgtgg   660
cgtggcgatt aacgcaccgg cggcagttgt acctatccgt accattcaca atatttcgct   720
gaatcctaac tttggcggcg aagtaatggt gattggcctg ggttgtgaaa agttgcagcc   780
tgagcgcctg ctgactggaa cggatgatgt gcaagctatt ccagtagaaa gcgccagcat   840
tgtcagtttg caggatgaaa agcatgtcgg ttttcagtcc atggtcgagg atatttttgca   900
gatcgccgaa cgccatctac aaaaactgaa tcaacggcag cgagaaacct gcccggcttc   960
agaactggtc gttggtatgc agtgcggtgg cagcgatgcg ttttctggtg taacggcaaa  1020
cccggcggtt ggctatgcgt ctgatctact ggtgcgctgc ggcgcaacgg tgatgttttc  1080
agaagtaacg gaagtgcgtg acgcgatcca tctgctgaca ccacgcgcag tgaacgaaga  1140
```

```
ggtcggcaaa cggctgctgg aggagatgga gtggtacgat aactatctca atatgggaaa    1200
aaccgaccgc agcgccaacc cttcgccggg caacaagaaa ggcggtctgg caaacgtggt    1260
agagaaggca ctcggctcca ttgctaaatc gggtaaaagc gcaattgttg aagtgctgtc    1320
gcccggtcaa cgcccgacta aacgcggatt aatttacgcc gcgacgccag ccagcgattt    1380
tgtctgtggc acgcaacagg tggcttcggg tatcacagtg caagtgttta cgaccggtcg    1440
tggtacgccg tacggcctga tggcggtacc cgtcattaaa atggcaaccc gcaccgagct    1500
ggcgaaccgc tggtttgatt taatggatat taatgcgggc accatcgcta ccggcgaaga    1560
aactattgaa gaggtgggct ggaagttgtt ccactttatt ctcgacgtcg ccagcgggaa    1620
gaagaaaacc ttctcggatc aatgggggct gcataaccag ctggcggtgt taacccggc    1680 accggtgacc tga                                                      1693
```

<210> SEQ ID NO 5
<211> LENGTH: 1045
<212> TYPE: DNA
<213> ORGANISM: Escherichia coli

<400> SEQUENCE: 5

```
tcgccatttt tgctatcatg cctgcataca taaacgacaa acagtatgc agagggaaaa      60 ttgacggcta gctcagtcct aggtacagtg ctagctaagt aggtacgtaa ggaggtgata    120
aatgggttcc accagaaagg ggatgctgaa cgttctgatt gccgccgtgt tgtggggaag    180 ttcagggggtc tgcgcgcaat acatcatgga gcaaagccag atgtcgtcgc agttttttgac    240 tatgacgcgt ttgatattcg ccggtttgat tctactgacg ctgtcatttg ttcatggcga    300
taaaatcttt tctattatta acaatcataa agatgccatt agcctgctga ttttttccgt    360
ggttggcgcg ctaactgtac agctcacttt tttgctaacc atcgaaaaat cgaacgcagc    420
cacggcaacg gtgctgcaat cctctcacc gacgattatc gtcgcctggt tctcactggt    480
gcgtaaatcg cgcccgggca ttctggtttt ctgcgctatt ttgacatcgc tggtcgggac    540
ttttttattg gtgacacacg gtaatccgac gtcattatcg atctctcctg ccgcgttgtt    600
ctggggcatt gcctcggcat tgctgctgc attctatacc acctatccct caacgctaat    660
tgcccgctat ggcacgttac cagtcgtcgg ctggagtatg ctgattggcg gtctgattct    720
gttgcctttt tatgccagac aaggaacaaa ctttgtcgtt aacggcagtt tgattctggc    780 gttttttttat tggtggtca ttggtacgtc cctgacattt agtctgtacc tgaaaggagc    840
acaattaatt ggcggtccaa aagccagcat tttgagctgt gcagaaccat taagtagcgc    900
gctactctct ttgctgttgc tggggatcac gttcacatta ccggactggc tgggaacgct    960
gctgattctg tcatcggtga ttttgatttc aatggattcc cgtcgccgcg ccagaaaaat   1020
aaatcgtccg gcgcggcata agtga                                         1045
```

<210> SEQ ID NO 6
<211> LENGTH: 14
<212> TYPE: PRT
<213> ORGANISM: Escherichia coli

<400> SEQUENCE: 6

```
Met Val Ser Glu Thr Lys Thr Thr Glu Ala Pro Gly Leu Arg
1               5                   10
```

<210> SEQ ID NO 7
<211> LENGTH: 580

<212> TYPE: DNA
<213> ORGANISM: Escherichia coli

<400> SEQUENCE: 7

```
tatcttgcag cgataagtgc ttacagtaat ctgtaggaaa gttaactacg gatgtacatt      60
ttgacggcta gctcagtcct aggtacagtg ctagctaagt aggtacgtaa ggaggtgata     120
aatggaactg acgactcgca ctttacctgc gcggaaacat attgcgctgg tggcacacga     180
tcactgcaaa caaatgctga tgagctgggt ggaacggcat caaccgttac tggaacaaca     240
cgtactgtat gcaacaggca ctaccggtaa cttaatttcc cgcgcgaccg gcatgaacgt     300
caacgcgatt ttgagtggcc aatgggggg tgaccagcag gttggcgcat tgatctcaga      360
agggaaaatt gatgtattga ttttcttctg ggatccacta aatgccgtgc cgcacgatcc     420
tgacgtgaaa gccttgctgc gtctggcgac ggtatggaac attccggtcg ccaccaacgt     480
ggcaacggca gacttcataa tccagtcgcc gcatttcaac gacgcggtcg atattctgat     540
ccccgattat cagcgttatc tcgcggaccg tctgaagtaa                            580
```

<210> SEQ ID NO 8
<211> LENGTH: 540
<212> TYPE: PRT
<213> ORGANISM: Escherichia coli

<400> SEQUENCE: 8

```
Met Arg Val Asn Asn Gly Leu Thr Pro Gln Glu Leu Glu Ala Tyr Gly
1               5                   10                  15

Ile Ser Asp Val His Asp Ile Val Tyr Asn Pro Ser Tyr Asp Leu Leu
            20                  25                  30

Tyr Gln Glu Glu Leu Asp Pro Ser Leu Thr Gly Tyr Glu Arg Gly Val
        35                  40                  45

Leu Thr Asn Leu Gly Ala Val Ala Val Asp Thr Gly Ile Phe Thr Gly
    50                  55                  60

Arg Ser Pro Lys Asp Lys Tyr Ile Val Arg Asp Asp Thr Thr Arg Asp
65                  70                  75                  80

Thr Phe Trp Trp Ala Asp Lys Gly Lys Gly Lys Asn Asp Asn Lys Pro
                85                  90                  95

Leu Ser Pro Gln Thr Trp Gln His Leu Lys Gly Leu Val Thr Arg Gln
            100                 105                 110

Leu Ser Gly Lys Arg Leu Phe Val Val Asp Ala Phe Cys Gly Ala Asn
        115                 120                 125

Pro Asp Thr Arg Leu Ser Val Arg Phe Ile Thr Glu Val Ala Trp Gln
    130                 135                 140

Ala His Phe Val Lys Asn Met Phe Ile Arg Pro Ser Asp Glu Glu Leu
145                 150                 155                 160

Ala Gly Phe Lys Pro Asp Phe Ile Val Met Asn Gly Ala Lys Cys Thr
                165                 170                 175

Asn Pro Gln Trp Lys Glu Gln Gly Leu Asn Ser Glu Asn Phe Val Ala
            180                 185                 190

Phe Asn Leu Thr Glu Arg Met Gln Leu Ile Gly Gly Thr Trp Tyr Gly
        195                 200                 205

Gly Glu Met Lys Lys Gly Met Phe Ser Met Met Asn Tyr Leu Leu Pro
    210                 215                 220

Leu Lys Gly Ile Ala Ser Met His Cys Ser Ala Asn Val Gly Glu Lys
225                 230                 235                 240

Gly Asp Val Ala Val Phe Phe Gly Leu Ser Gly Thr Gly Lys Thr Thr
```

```
                245                 250                 255
Leu Ser Thr Asp Pro Lys Arg Arg Leu Ile Gly Asp Asp Glu His Gly
        260                 265                 270

Trp Asp Asp Gly Val Phe Asn Phe Glu Gly Gly Cys Tyr Ala Lys
            275                 280             285

Thr Ile Lys Leu Ser Lys Glu Ala Glu Pro Glu Ile Tyr Asn Ala Ile
        290                 295                 300

Arg Arg Asp Ala Leu Leu Glu Asn Val Thr Val Arg Glu Asp Gly Thr
305                 310                 315                 320

Ile Asp Phe Asp Asp Gly Ser Lys Thr Glu Asn Thr Arg Val Ser Tyr
                325                 330                 335

Pro Ile Tyr His Ile Asp Asn Ile Val Lys Pro Val Ser Lys Ala Gly
            340                 345                 350

His Ala Thr Lys Val Ile Phe Leu Thr Ala Asp Ala Phe Gly Val Leu
        355                 360                 365

Pro Pro Val Ser Arg Leu Thr Ala Asp Gln Thr Gln Tyr His Phe Leu
370                 375                 380

Ser Gly Phe Thr Ala Lys Leu Ala Gly Thr Glu Arg Gly Ile Thr Glu
385                 390                 395                 400

Pro Thr Pro Thr Phe Ser Ala Cys Phe Gly Ala Ala Phe Leu Ser Leu
                405                 410                 415

His Pro Thr Gln Tyr Ala Glu Val Leu Val Lys Arg Met Gln Ala Ala
            420                 425                 430

Gly Ala Gln Ala Tyr Leu Val Asn Thr Gly Trp Asn Gly Thr Gly Lys
        435                 440                 445

Arg Ile Ser Ile Lys Asp Thr Arg Ala Ile Ile Asp Ala Ile Leu Asn
    450                 455                 460

Gly Ser Leu Asp Asn Ala Glu Thr Phe Thr Leu Pro Met Phe Asn Leu
465                 470                 475                 480

Ala Ile Pro Thr Glu Leu Pro Gly Val Asp Thr Lys Ile Leu Asp Pro
                485                 490                 495

Arg Asn Thr Tyr Ala Ser Pro Glu Gln Trp Gln Glu Lys Ala Glu Thr
            500                 505                 510

Leu Ala Lys Leu Phe Ile Asp Asn Phe Asp Lys Tyr Thr Asp Thr Pro
        515                 520                 525

Ala Gly Ala Ala Leu Val Ala Ala Gly Pro Lys Leu
        530                 535                 540

<210> SEQ ID NO 9
<211> LENGTH: 1609
<212> TYPE: DNA
<213> ORGANISM: Escherichia coli

<400> SEQUENCE: 9
gctcgcgaat aatccgatta cggctacgct tctaatgttc cccttgaatg gagtcgaaga      60
ttgacggcta gctcagtcct aggtacagtg ctagctaagt aggtacgtaa ggaggtgata    120
aatgcgtaat cccacgctgt tacaatgttt tcactggtat taccccggaag gcggtaagct    180 ctggcctgaa ctggccgagc gcgccgacgg ttttaatgat attggtatca atatggtctg    240
gttgccgccc gcctataaag gcgcatcggg cgggtattcg gtcggctacg actcctatga    300
tttatttgat ttaggcgagt ttgatcagaa aggcagcatc cctactaaat atggcgataa    360
agcacaactg ctggccgcca ttgatgctct gaaacgtaat gacattgcgg tgctgttgga    420
tgtggtagtc aaccacaaaa tgggcgcgga tgaaaaagaa gctattcgcg tgcagcgtgt    480
```

| | |
|---|---|
| aaatgctgat gaccgtacgc aaattgacga agaaatcatt gagtgtgaag gctggacgcg | 540 |
| ttacaccttc cccgcccgtg ccgggcaata ctcgcagttt atctgggatt tcaaatgttt | 600 |
| tagcggtatc gaccatatcg aaaaccctga cgaagatggc attttttaaaa ttgttaacga | 660 |
| ctacaccggc gaaggctgga acgatcaggt tgatgatgaa ttaggtaatt tcgattatct | 720 |
| gatgggcgag aatatcgatt ttcgcaatca tgccgtgacg aagagatta aatactgggc | 780 |
| gcgctgggta tggaacaaa cgcaatgcga cggttttcgt cttgatgcgg tcaaacatat | 840 |
| tccagcctgg ttttataaag agtggatcga acacgtacag gaagttgcgc caaagccgct | 900 |
| gtttattgtg gcggagtact ggtcgcatga agttgataag ctgcaaacgt atattgatca | 960 |
| ggtggaaggc aaaaccatgc tgtttgatgc gccgctgcag atgaaattcc atgaagcatc | 1020 |
| gcgcatgggg cgcgactacg acatgacgca gattttcacg ggtacattag tggaagccga | 1080 |
| tcctttccac gccgtgacgc tcgttgccaa tcacgacacc caaccgttgc aagccctcga | 1140 |
| agcgccggtc gaaccgtggt ttaaaccgct ggcgtatgcc ttaattttgt tgcgggaaaa | 1200 |
| tggcgttcct tcggtattct atccggacct ctacggtgcg cattacgaag atgtcggtgg | 1260 |
| tgacgggcaa acctatccga tagatatgcc aataatcgaa cagcttgatg agttaattct | 1320 |
| cgcccgtcag cgtttcgccc acggtgtaca gacgttattt ttcgaccatc gaactgcat | 1380 |
| tgcctttagc cgcagtggca ccgacgaatt cccggctgc gtggtggtca tgtcgaacgg | 1440 |
| ggatgatggc gaaaaaacca ttcatctggg agagaattac ggcaataaaa cctggcgtga | 1500 |
| tttttctgggg aaccggcaag agagagtagt gaccgacgaa aacggcgaag caaccttctt | 1560 |
| ttgcaacggc ggcagcgtca gcgtgtgggt tatcgaagag gtgatttaa | 1609 |

<210> SEQ ID NO 10
<211> LENGTH: 14
<212> TYPE: PRT
<213> ORGANISM: Escherichia coli

<400> SEQUENCE: 10

Met Arg Asn Pro Thr Leu Leu Gln Cys Phe His Trp Tyr Tyr
1               5                   10

<210> SEQ ID NO 11
<211> LENGTH: 4
<212> TYPE: PRT
<213> ORGANISM: Escherichia coli

<400> SEQUENCE: 11

Met Asn Thr Ala
1

<210> SEQ ID NO 12
<211> LENGTH: 2521
<212> TYPE: DNA
<213> ORGANISM: Escherichia coli

<400> SEQUENCE: 12

| | |
|---|---|
| agaaaccgtg ttgaactctg aaagccagt ctttagatgc gccaggatgc agaggtaatc | 60 |
| ttgacggcta gctcagtcct aggtacagtg ctagctaagt aggtacgtaa ggaggtgata | 120 |
| aatgaagcta accgatgcgg ataatgccgc cgatggcatt ttttcccg cccttgagca | 180 |
| aaatatgatg ggtgcggtgt taattaacga aaatgatgaa gtgatgtttt tcaacccgc | 240 |
| cgcagagaag ctctggggat acaaacgtga agaagtcatt ggcaataaca ttgatatgct | 300 |

```
gattccgcgg gatttgcgtc ctgcgcatcc tgaatacatt cgtcacaacc gtgaaggcgg      360
taaagcgcgt gttgagggga tgagtcggga gctgcagctg gagaaaaaag acggcagtaa      420
aatctggacc cgttttgcgc tatcgaaagt gagcgccgag gggaaagttt attacctggc      480
gctggtacgg gatgccagcg tagaaatggc gcaaaaagaa cagacccgac aattgattat      540
tgccgttgac catctcgacc gaccggtgat tgtcctcgat ccggaacgcc atattgtgca      600
gtgcaatcgc gcatttaccg aaatgtttgg ttactgcatt agcgaagcca gcggtatgca      660
gcccgataca ctcctgaaca ttcctgaatt ccctgccgat aaccgcattc gtttacaaca      720
gttgctatgg aaaaccgccc gcgatcagga cgaatttctg ctgttgacgc gcaccggtga      780
aaaaatctgg attaaagcct ctatcagccc ggtttatgac gtgctcgcgc atctgcagaa      840
cctggtaatg actttctcgg atatcaccga agaacggcag attcgccagc ttgaaggcaa      900
tattctcgcc gccatgtgca gcagcccgcc atttcatgaa atggggaaa tcatttgtcg        960
taacatcgaa tctgtactca acgaatcgca tgtttcgctg ttcgcactgc gcaacgggat      1020
gccgatacac tgggcgtcat cttcccacgg tgcagaaatt caaaatgcgc aaagctggtc      1080
agcgaccatt cgtcagcgtg atggcgcgcc tgcgggatc ctgcaaatta aaacctcgtc        1140
aggagcagaa accagcgcct ttatcgaacg cgtggcagat atcagccagc atatggccgc      1200
gctggcgctg gaacaggaaa aaagccgtca gcatattgaa caactcatcc aatttgatcc      1260
gatgaccggt ctgccaaatc gcaataacct gcacaattac ctcgatgacc tggtcgacaa      1320
agccgtctct cccgtggtgt atctcatcgg tgttgaccat attcaggatg tgattgatag      1380
ccttggctat gcgtgggccg atcaggcatt gctggaagtg gtcaatcgct ttcgtgaaaa      1440
actcaaaccg gatcagtatc tctgtcgtat cgaaggtacg cagtttgtcc tcgtgagcct      1500
cgaaaacgac gtcagtaaca ttacccaaat cgccgatgag ctacgaaatg tggtcagcaa      1560
gccgataatg attgacgata aacccttccc gcttaccttg agtattggca tcagctacga      1620
cctgggtaaa aaccgcgatt acttgctctc cactgctcac aatgcaatgg attatattcg      1680
caagaatggc ggtaacggct ggcagttctt cagcccggcg atgaacgaaa tggtaaaaga      1740
gcgtttggtt ttaggcgcag cgctgaaaga agcgattagc aataaccaac tgaaaactggt      1800
ttaccagccg caaatcttcg cagaaacggg tgaactgtac ggcatcgaag cccttgctcg      1860
ctggcacgat cccctgcatg gtcatgtgcc cccttcacgg tttattcctc tcgcagaaga      1920
gattggtgaa atcgaaaata ttgggcgctg gtcatcgcg gaagcttgcc gtcagttagc        1980
agaatgcgct agccagaata ttcatatccc ggcgttatcc gtgaacttgt cggcgctgca      2040
ctttcgcagt aatcaactgc ctaatcaggt gtctgatgca atgcacgcct ggggtattga      2100
cggccaccag ctgacggtag aaatcacgga aagcatgatg atggaacacg ataccgaaat      2160
ctttaagcgc attcagatcc tgcgtgatat gggcgtgggc ttatcggtag atgattttgg      2220
tacgggcttt tccggattat cccgcttagt cagtcttccg gtaacggaaa tcaaaattga      2280
caaaagttttt gtcgatcgtt gtctgaccga aaaacgcatc cttgccttac ttgaagccat      2340
taccagcatt gggcaaagcc tcaatttaac cgtcgtggcg aaggcgtcg aaaccaaaga        2400
gcaatttgag atgctacgca agatccactg tcgcgttatt cagggatatt tcttttcccg      2460
cccccctaccc gccgaagaaa ttccaggctg atgagcagc gtgttaccgc tgaaaatctg       2520
a                                                                     2521
```

<210> SEQ ID NO 13
<211> LENGTH: 454

<212> TYPE: DNA
<213> ORGANISM: Escherichia coli

<400> SEQUENCE: 13

```
ggtgagttga gttcaaactg tagtacaatt ctctccagtt tgaacaggaa agaatatgct      60
ttgacggcta gctcagtcct aggtacagtg ctagctaagt aggtacgtaa ggaggtgata     120
aatgaaccct tatatttatc ttggtggtgc aatacttgca gaggtcattg gtacaacctt     180
aatgaagttt tcagaaggtt ttacacggtt atggccatct gttggtacaa ttatttgtta     240
ttgtgcatca ttctggttat tagctcagac gctggcttat attcctacag ggattgctta     300
tgctatctgg tcaggagtcg gtattgtcct gattagctta ctgtcatggg gattttttcgg    360
ccaacggctg gacctgccag ccattatagg catgatgttg atttgtgccg gtgtgttgat     420
tattaattta ttgtcacgaa gcacaccaca ttaa                                 454
```

<210> SEQ ID NO 14
<211> LENGTH: 970
<212> TYPE: DNA
<213> ORGANISM: Escherichia coli

<400> SEQUENCE: 14

```
atgcagcggc tggggatctc ggttcgcgag gtgttgtaat ctgcttttgc aggagtatgc      60
ttgacggcta gctcagtcct aggtacagtg ctagctaagt aggtacgtaa ggaggtgata     120
aatgagaaac aaactctctt tcgacttgca gttgagcgcc agaaaagcgg caatcgctga     180
acggattgcc gcccataaaa ttgcccgcag taaagtgtcg gtcttttaa tggcgatgtc      240
cgctggcgtg tttatggcga tcggatttac tttttacctt tccgttatcg ccgatgcccc     300
gtcttcacag gcattaaccc atctggtggg cggcctttgc tttacactcg ctttattt      360
gctggcggtt tgcggcacca gcctgttcac ctcgtcggta atgacggtga tggcaaaaag    420
tcggggcgtt attagttggc gaacttggct gattaacgca cttctggtgg cctgcggtaa     480
tctggcaggt attgcctgtt tcagtttgtt aatctggttt tccgggctgg tgatgagtga     540
aaacgcgatg tggggagtcg cggttttaca ctgcgccgag ggcaaaatgc atcatacatt     600
tactgaatct gtcagcctcg gcattatgtg caatctgatg gtttgcctgg cgctgtggat     660
gagttattgc gggcgttcgt tatgcgacaa atcgtcgcc atgatttgc ccatcaccct       720
gtttgtcgcc agtggctttg agcactgtat cgccaatttg tttgtgattc cgttcgccat     780
tgccattcgc catttcgccc ctcccccctt ctggcagctg cgcacagta gcgcagacaa      840
ttttccggca ctgacggtca gccatttat taccgccaat ctgctcccgg tgatgctggg     900
taatattatc ggcggtgcgg tgctggtgag tatgtgttat cgggctattt atttacgtca     960
ggaaccctga                                                            970
```

<210> SEQ ID NO 15
<211> LENGTH: 2794
<212> TYPE: DNA
<213> ORGANISM: Escherichia coli

<400> SEQUENCE: 15

```
atgaagccgg cgaatgccgg cttttttaat gcgataattt aatcttatgg gtggcgcaca      60
ttgacggcta gctcagtcct aggtacagtg ctagctaagt aggtacgtaa ggaggtgata     120
aatgaatacc cttccagaac agtacgcaaa caccgctctc cccacccgc ccggtcaacc      180
gcaaaatcca tgcgtctggc cccgtgatga attaaccgtc ggtgggataa aagcccatat     240
```

```
cgatactttc cagcgttggc tgggtgatgc ctttgacaat gggatctctg cagaacagtt      300
gattgaggcg cgcaccgagt ttatcgacca gctcctgcaa cgattatgga ttgaagcggg      360
attcagccag attgccgacc tggcattggt cgccgtcggt ggctacggtc gtggcgagct      420
gcatccactt tcagacgtcg atttactgat tttaagccgt aaaaagctcc cggacgatca      480
ggcgcaaaaa gtgggcgagc tgttaacgct gctctgggat gtaaagctgg aagtcggtca      540
tagcgtgcgc acgcttgaag agtgcatgct ggaagggtta tcggatttaa ccgtcgccac      600
caatttaatc gaatcccgct tattaattgg cgatgttgcg ctgttcctcg aactgcaaaa      660
acatattttc agcgaaggat tctggccttc cgacaagttc tacgcggcga agttgaaga      720 acagaaccag cgccatcagc gttaccatgg caccagctac aaccttgaac cagacatcaa      780
aagcagccct ggcggcttgc gcgatatcca cactctgcaa tgggtggccc gccgtcattt      840
tggcgcaaca tcgctggatg aaatggtcgg gtttggcttc ttaacctcag cggagcgggc      900
ggaattaaac gaatgtctgc atatattgtg gcgtattcgc tttgccctgc atctggtcgt      960
cagccgttac gataatcgcc tgttattcga tcgccagctt agcgtcgccc agcgtctgaa     1020
ttacagtggt gaaggtaacg aaccggtcga gcggatgatg aaggattact ccgcgttac      1080 acgccgcgtc agtgaactca accagatgct gctgcaactg ttcgatgaag ccatcctcgc     1140
ccttcccgcc gacgaaaaac cacgtccaat cgacgatgag tttcagctac gcggtacgct     1200
aatcgacctg cgtgatgaaa cactatttat gcgccagccg gaagccatct tgcgtatgtt     1260
ctacaccatg gtgcacaaca gtgcgatcac cggcatttac tccaccacgc tgcgccagtt     1320
acgccatgcc cgtcgccatc tgcaacaacc gctgtgtaat attccggaag cacgaaaact     1380 gttttttgagc attctgcgtc accccggagc ggtgcggcgc gggctattgc caatgcatcg     1440
ccatagcgtg ctcggcgcgt atatgccgca atggtcgcat atcgtcgggc agatgcagtt     1500
tgatctgttc cacgcctaca cggtggatga acatactatc cgcgtgatgc tgaaactgga     1560
gagttttgcc agtgaagaaa cgcgccagcc ccatccgttg tgtgtggacg tctgccgcg      1620 cctgccgtca actgagctga ttttcatcgc cgcgctgttt cacgatatcg ccaaaggacg     1680
cggcggcgac cactccattc tcggtgctca ggatgtagtg cattttgccg aactccacgg     1740
gctgaactca cgcgaaacac agctggtcgc ctggctggtt cgccagcacc tgttgatgtc     1800
ggtgaccgcc caacgccgcg atattcagga cccggaagtc atcaagcagt ttgccgaaga     1860
agtgcaaacg gaaaatcgtc tgcgctatct ggtatgcctg actgtggctg acatttgcgc     1920
caccaacgaa acgctgtgga atagctggaa gcaaagtctg ttgcgtgagc tctactttgc     1980
caccgaaaag cagctacgac gcggaatgca aaacacgccg gatatgcgcg aacgggttcg     2040
ccatcaccaa ctccaggcac tggcactact gcgcatggat aacatcgacg aagaggcgct     2100
gcaccaaatt tggtcacgct gtcgtgctaa ctattttgtc cgccatagcc caaatcaact     2160
ggcctggcat gcccgccatt tattacagca tgatttaagc aaaccgctgg tattgcttag     2220
cccgcaggct acgcgtggag gcaccgagat ttttatctgg agcccggacc gcccttatct     2280
gtttgccgcc gtctgtgccg aattagaccg ccgcaattta agtgttcacg acgcacaaat     2340
tttcaccact cgcgacggta tggcgatgga tacctttatc gtgctggaac ccgatggcaa     2400
cccgctgtcc gcagatcgtc atgaggttat tcggtttggt ctggagcaag tactgacgca     2460
aagtagctgg cagccaccgc agcccgtccg ccaacccgcc aaattacgcc attttactgt     2520
tgaaaccgaa gtaacgtttt tgccgaccca taccgaccgc aaatcgttcc tcgaactgat     2580
cgccctcgac caacctggac tgctggcgcg agtcgggaaa atttttgccg atctgggaat     2640
```

```
ttcgcttcat ggtgcccgaa ttacaaccat tggcgagcga gtagaagatt tattcataat    2700
tgccaccgct gaccggcgtg cgcttaataa cgagttgcag caggaagtgc atcagcggtt    2760
gacagaggcc ctcaatccaa acgataaagg gtga                                2794

<210> SEQ ID NO 16
<211> LENGTH: 14
<212> TYPE: PRT
<213> ORGANISM: Escherichia coli

<400> SEQUENCE: 16

Met Lys Pro Leu Ser Ser Pro Leu Gln Gln Tyr Trp Gln Thr
1               5                   10

<210> SEQ ID NO 17
<211> LENGTH: 538
<212> TYPE: DNA
<213> ORGANISM: Escherichia coli

<400> SEQUENCE: 17
ctcggtttga gttaatcgcc aattaaaaag gttaatgaca tgcgagagac agtcgaaatt     60
ttgacggcta gctcagtcct aggtacagtg ctagctaagt aggtacgtaa ggaggtgata   120
aatgcgttat cccgtcactc ttacacccgc gccggaaggc ggttatatgg tttcttttgt   180
ggatatccct gaagcgttga cccagggcga aactgtcgct gaagcgatgg aagcggcaaa   240
agatgcttta ctgaccgcat ttgatttttta ttttgaagat aacgagctta ccctttacc   300 ttcgccatta aatagtcacg atcactttat tgaagtacct ttgagcgtcg cctctaaggt   360
attgctgtta aatgcttttt tacagtcaga aatcactcag caagagttag ccaggcgaat   420
tggcaaacct aaacaggaga ttactcgcct atttaacttg catcatgcga caaaaatcga   480
cgccgtccag ctcgcggcaa aggcgcttgg caaagagtta tcgctggtga tggtttaa    538

<210> SEQ ID NO 18
<211> LENGTH: 2401
<212> TYPE: DNA
<213> ORGANISM: Escherichia coli

<400> SEQUENCE: 18
tgggcagggg ctgttgccca cacactttat ttgtgaacgt tacgtgaaag gaacaaccaa     60
ttgacggcta gctcagtcct aggtacagtg ctagctaagt aggtacgtaa ggaggtgata   120
aatggatgac cagttaaaac aaagtgcact tgatttccat gaatttccag ttccagggaa   180
aatccaggtt ctccaaccca gcctctggca acacagcgc gatctggcgc tggcctactc   240
accaggcgtt gccgcacctt gtcttgaaat cgaaaaagac ccgttaaaag cctacaaata   300
taccgcccga ggtaacctgg tggcggtgat ctctaacggt acggcggtgc tggggttagg   360
caacattggc gcgctggcag gcaaaccggt gatggaaggc aagggcgttc tgtttaagaa   420
attcgccggg attgatgtat ttgacattga agttgacgaa ctcgacccgg acaaatttat   480
tgaagttgtc gccgcgctcg aaccaacctt cggcggcatc aacctcgaag acattaaagc   540
gccagaatgt ttctatattg aacagaaact gcgcgagcgg atgaatattc cggtattcca   600
cgacgatcag cacggcacgg caattatcag cactgccgcc atcctcaacg gcttgcgcgt   660
ggtggagaaa aacatctccg acgtgcggat ggtggtttcc ggcgcgggtg ccgcagcaat   720
cgcctgtatg aacctgctgg tagcgctggg tctgcaaaaa cataacatcg tggtttgcga   780
ttcaaaaggc gttatctatc agggccgtga gccaaacatg gcggaaacca agccgcata    840
```

```
tgcggtggtg gatgacggca aacgtaccct cgatgatgtg attgaaggcg cggatatttt    900
cctgggctgt tccggcccga aagtgctgac ccaggaaatg gtgaagaaaa tggctcgtgc    960
gccaatgatc ctggcgctgg cgaacccgga accggaaatt ctgccgccgc tggcgaaaga   1020
agtgcgtccg gatgccatca tttgcaccgg tcgttctgac tatccgaacc aggtgaacaa   1080
cgtcctgtgc ttcccgttca tcttccgtgg cgcgctggac gttggcgcaa ccgccatcaa   1140
cgaagagatg aaactggcgg cggtacgtgc gattgcagaa ctcgcccatg cggaacagag   1200
cgaagtggtg gcttcagcgt atggcgatca ggatctgagc tttggtccgg aatacatcat   1260
tccaaaaccg tttgatccgc gcttgatcgt taagatcgct cctgcggtcg ctaaagccgc   1320
gatggagtcg ggcgtggcga ctcgtccgat tgctgatttc gacgtctaca tcgacaagct   1380
gactgagttc gtttacaaaa ccaacctgtt tatgaagccg attttctccc aggctcgcaa   1440
agcgccgaag cgcgttgttc tgccggaagg ggaagaggcg cgcgttctgc atgccactca   1500
ggaactggta acgctgggac tggcgaaacc gatccttatc ggtcgtccga acgtgatcga   1560
aatgcgcatt cagaaactgg gcttgcagat caaagcgggc gttgattttg agatcgtcaa   1620
taacgaatcc gatccgcgct ttaaagagta ctggaccgaa tacttccaga tcatgaagcg   1680
tcgcggcgtc actcaggaac aggcgcagcg ggcgctgatc agtaacccga cagtgatcgg   1740
cgcgatcatg gttcagcgtg gggaagccga tgcaatgatt tgcggtacgg tgggtgatta   1800
tcatgaacat tttagcgtgg tgaaaaatgt ctttggttat cgcgatggcg ttcacaccgc   1860
aggtgccatg aacgcgctgc tgctgccgag tggtaacacc tttattgccg atacatatgt   1920
taatgatgaa ccggatgcag aagagctggc ggagatcacc ttgatggcgg cagaaactgt   1980
ccgtcgtttt ggtattgagc cgcgcgttgc tttgttgtcg cactccaact ttggttcttc   2040
tgactgcccg tcgtcgagca aaatgcgtca ggcgctggaa ctggtcaggg aacgtgcacc   2100
agaactgatg attgatggtg aaatgcacgg cgatgcagcg ctggtggaag cgattcgcaa   2160
cgaccgtatg ccggacagct cttttgaaag gttccgccaat attctggtga tgccgaacat   2220
ggaagctgcc cgcattagtt acaacttact gcgtgtttcc agctcggaag gtgtgactgt   2280
cggcccggtg ctgatgggtg tggcgaaacc ggttcacgtg ttaacgccga tcgcatcggt   2340
gcgtcgtatc gtcaacatgg tggcgctggc cgtggtagaa gcgcaaaccc aaccgctgta   2400
a                                                                   2401
```

<210> SEQ ID NO 19
<211> LENGTH: 127
<212> TYPE: PRT
<213> ORGANISM: Escherichia coli

<400> SEQUENCE: 19

Met Ser Arg Arg Asn Thr Asp Ala Ile Thr Ile His Ser Ile Leu Asp
1               5                   10                  15

Trp Ile Glu Asp Asn Leu Glu Ser Pro Leu Ser Leu Glu Lys Val Ser
            20                  25                  30

Glu Arg Ser Gly Tyr Ser Lys Trp His Leu Gln Arg Met Phe Lys Lys
        35                  40                  45

Glu Thr Gly His Ser Leu Gly Gln Tyr Ile Arg Ser Arg Lys Met Thr
    50                  55                  60

Glu Ile Ala Gln Lys Leu Lys Glu Ser Asn Glu Pro Ile Leu Tyr Leu
65                  70                  75                  80

Ala Glu Arg Tyr Gly Phe Glu Ser Gln Gln Thr Leu Thr Arg Thr Phe

```
            85                  90                  95
Lys Asn Tyr Phe Asp Val Pro Pro His Lys Asp Arg Met Thr Asn Met
            100                 105                 110

Gln Gly Glu Ser Arg Phe Leu His Pro Leu Asn His Tyr Asn Ser
            115                 120                 125
```

<210> SEQ ID NO 20
<211> LENGTH: 810
<212> TYPE: PRT
<213> ORGANISM: Escherichia coli

<400> SEQUENCE: 20

```
Met Ser Val Ile Ala Gln Ala Gly Ala Lys Gly Arg Gln Leu His Lys
1               5                   10                  15

Phe Gly Gly Ser Ser Leu Ala Asp Val Lys Cys Tyr Leu Arg Val Ala
                20                  25                  30

Gly Ile Met Ala Glu Tyr Ser Gln Pro Asp Asp Met Met Val Val Ser
                35                  40                  45

Ala Ala Gly Ser Thr Thr Asn Gln Leu Ile Asn Trp Leu Lys Leu Ser
        50                  55                  60

Gln Thr Asp Arg Leu Ser Ala His Gln Val Gln Gln Thr Leu Arg Arg
65                  70                  75                  80

Tyr Gln Cys Asp Leu Ile Ser Gly Leu Leu Pro Ala Glu Glu Ala Asp
                85                  90                  95

Ser Leu Ile Ser Ala Phe Val Ser Asp Leu Glu Arg Leu Ala Ala Leu
                100                 105                 110

Leu Asp Ser Gly Ile Asn Asp Ala Val Tyr Ala Glu Val Val Gly His
                115                 120                 125

Gly Glu Val Trp Ser Ala Arg Leu Met Ser Ala Val Leu Asn Gln Gln
            130                 135                 140

Gly Leu Pro Ala Ala Trp Leu Asp Ala Arg Glu Phe Leu Arg Ala Glu
145                 150                 155                 160

Arg Ala Ala Gln Pro Gln Val Asp Glu Gly Leu Ser Tyr Pro Leu Leu
                165                 170                 175

Gln Gln Leu Leu Val Gln His Pro Gly Lys Arg Leu Val Val Thr Gly
                180                 185                 190

Phe Ile Ser Arg Asn Asn Ala Gly Glu Thr Val Leu Leu Gly Arg Asn
                195                 200                 205

Gly Ser Asp Tyr Ser Ala Thr Gln Ile Gly Ala Leu Ala Gly Val Ser
            210                 215                 220

Arg Val Thr Ile Trp Ser Asp Val Ala Gly Val Tyr Ser Ala Asp Pro
225                 230                 235                 240

Glu Lys Val Lys Asp Ala Cys Leu Leu Pro Leu Leu Arg Leu Asp Glu
                245                 250                 255

Ala Ser Glu Leu Ala Arg Leu Ala Ala Pro Val Leu His Ala Arg Thr
                260                 265                 270

Leu Gln Pro Val Ser Gly Ser Glu Ile Asp Leu Gln Leu Arg Cys Ser
                275                 280                 285

Tyr Thr Pro Asp Gln Gly Ser Thr Arg Ile Glu Arg Val Leu Ala Ser
                290                 295                 300

Gly Thr Gly Ala Arg Ile Val Thr Ser His Asp Asp Val Cys Leu Ile
305                 310                 315                 320

Glu Phe Gln Val Pro Ala Ser Gln Asp Phe Lys Leu Ala His Lys Glu
                325                 330                 335
```

-continued

Ile Asp Gln Ile Leu Lys Arg Ala Gln Val Arg Pro Leu Ala Val Gly
             340                 345                 350

Val His Asn Asp Arg Gln Leu Leu Gln Phe Cys Tyr Thr Ser Glu Val
             355                 360                 365

Ala Asp Ser Ala Leu Lys Ile Leu Asp Glu Ala Gly Leu Pro Gly Glu
             370                 375             380

Leu Arg Leu Arg Gln Gly Leu Ala Leu Val Ala Met Val Gly Ala Gly
385                 390                 395                 400

Val Thr Arg Asn Pro Leu His Cys His Arg Phe Trp Gln Gln Leu Lys
             405                 410                 415

Gly Gln Pro Val Glu Phe Thr Trp Gln Ser Asp Asp Gly Ile Ser Leu
             420                 425             430

Val Ala Val Leu Arg Thr Gly Pro Thr Glu Ser Leu Ile Gln Gly Leu
             435                 440             445

His Gln Ser Val Phe Arg Ala Glu Lys Arg Ile Gly Leu Val Leu Phe
         450                 455             460

Gly Lys Gly Asn Ile Gly Ser Arg Trp Leu Glu Leu Phe Ala Arg Glu
465                 470                 475                 480

Gln Ser Thr Leu Ser Ala Arg Thr Gly Phe Glu Phe Val Leu Ala Gly
             485                 490                 495

Val Val Asp Ser Arg Ser Leu Leu Ser Tyr Asp Gly Leu Asp Ala
             500                 505             510

Ser Arg Ala Leu Ala Phe Phe Asn Asp Glu Ala Val Glu Gln Asp Glu
         515                 520                 525

Glu Ser Leu Phe Leu Trp Met Arg Ala His Pro Tyr Asp Asp Leu Val
530                 535             540

Val Leu Asp Val Thr Ala Ser Gln Gln Leu Ala Asp Gln Tyr Leu Asp
545                 550                 555                 560

Phe Ala Ser His Gly Phe His Val Ile Ser Ala Asn Lys Leu Ala Gly
             565                 570                 575

Ala Ser Asp Ser Asn Lys Tyr Arg Gln Ile His Asp Ala Phe Glu Lys
             580                 585             590

Thr Gly Arg His Trp Leu Tyr Asn Ala Thr Val Gly Ala Gly Leu Pro
         595                 600             605

Ile Asn His Thr Val Arg Asp Leu Ile Asp Ser Gly Asp Thr Ile Leu
         610                 615             620

Ser Ile Ser Gly Ile Phe Ser Gly Thr Leu Ser Trp Leu Phe Leu Gln
625                 630                 635                 640

Phe Asp Gly Ser Val Pro Phe Thr Glu Leu Val Asp Gln Ala Trp Gln
             645                 650                 655

Gln Gly Leu Thr Glu Pro Asp Pro Arg Asp Asp Leu Ser Gly Lys Asp
             660                 665             670

Val Met Arg Lys Leu Val Ile Leu Ala Arg Glu Ala Gly Tyr Asn Ile
         675                 680                 685

Glu Pro Asp Gln Val Arg Val Glu Ser Leu Val Pro Ala His Cys Glu
         690                 695             700

Gly Gly Ser Ile Asp His Phe Phe Glu Asn Gly Asp Glu Leu Asn Glu
705                 710                 715                 720

Gln Met Val Gln Arg Leu Glu Ala Ala Arg Glu Met Gly Leu Val Leu
             725                 730                 735

Arg Tyr Val Ala Arg Phe Asp Ala Asn Gly Lys Ala Arg Val Gly Val
             740                 745             750

Glu Ala Val Arg Glu Asp His Pro Leu Ala Ser Leu Leu Pro Cys Asp

```
              755                 760                 765
Asn Val Phe Ala Ile Glu Ser Arg Trp Tyr Arg Asp Asn Pro Leu Val
    770                 775                 780
Ile Arg Gly Pro Gly Ala Gly Arg Asp Val Thr Ala Gly Ala Ile Gln
785                 790                 795                 800
Ser Asp Ile Asn Arg Leu Ala Gln Leu Leu
                805                 810

<210> SEQ ID NO 21
<211> LENGTH: 4
<212> TYPE: PRT
<213> ORGANISM: Escherichia coli

<400> SEQUENCE: 21

Met Pro Glu Gln
1

<210> SEQ ID NO 22
<211> LENGTH: 4
<212> TYPE: PRT
<213> ORGANISM: Escherichia coli

<400> SEQUENCE: 22

Met Asp Val Met
1

<210> SEQ ID NO 23
<211> LENGTH: 540
<212> TYPE: PRT
<213> ORGANISM: Escherichia coli

<400> SEQUENCE: 23

Met Arg Val Asn Asn Gly Leu Thr Pro Gln Glu Leu Glu Ala Tyr Gly
1               5                   10                  15
Ile Ser Asp Val His Asp Ile Val Tyr Asn Pro Ser Tyr Asp Leu Leu
            20                  25                  30
Tyr Gln Glu Glu Leu Asp Pro Ser Leu Thr Gly Tyr Glu Arg Gly Val
        35                  40                  45
Leu Thr Asn Leu Gly Ala Val Ala Val Asp Thr Gly Ile Phe Thr Gly
    50                  55                  60
Arg Ser Pro Lys Asp Lys Tyr Ile Val Arg Asp Asp Thr Thr Arg Asp
65                  70                  75                  80
Thr Phe Trp Trp Ala Asp Lys Gly Lys Gly Lys Asn Asp Asn Lys Pro
                85                  90                  95
Leu Ser Pro Glu Thr Trp Gln His Leu Lys Gly Leu Val Thr Arg Gln
            100                 105                 110
Leu Ser Gly Lys Arg Leu Phe Val Val Asp Ala Phe Cys Gly Ala Asn
        115                 120                 125
Pro Asp Thr Arg Leu Ser Val Arg Phe Ile Thr Glu Val Ala Trp Gln
    130                 135                 140
Ala His Phe Val Lys Asn Met Phe Ile Arg Pro Ser Asp Glu Glu Leu
145                 150                 155                 160
Ala Gly Phe Lys Pro Asp Phe Ile Val Met Asn Gly Ala Lys Cys Thr
                165                 170                 175
Asn Pro Gln Trp Lys Glu Gln Gly Leu Asn Ser Glu Asn Phe Val Ala
            180                 185                 190
Phe Asn Leu Thr Glu Arg Met Gln Leu Ile Gly Gly Thr Trp Tyr Gly
        195                 200                 205
```

Gly Glu Met Lys Lys Gly Met Phe Ser Met Met Asn Tyr Leu Leu Pro
210                 215                 220

Leu Lys Gly Ile Ala Ser Met Gly Cys Ser Ala Asn Val Gly Glu Lys
225                 230                 235                 240

Gly Asp Val Ala Val Phe Phe Gly Leu Ser Gly Thr Gly Lys Thr Thr
                245                 250                 255

Leu Ser Thr Asp Pro Lys Arg Arg Leu Ile Gly Asp Glu His Gly
                260                 265                 270

Trp Asp Asp Gly Val Phe Asn Phe Glu Gly Gly Cys Tyr Ala Lys
                275                 280                 285

Thr Ile Lys Leu Ser Lys Glu Ala Glu Pro Glu Ile Tyr Asn Ala Ile
290                 295                 300

Arg Arg Asp Ala Leu Leu Glu Asn Val Thr Val Arg Glu Asp Gly Thr
305                 310                 315                 320

Ile Asp Phe Asp Gly Ser Lys Thr Glu Asn Thr Arg Val Ser Tyr
                325                 330                 335

Pro Ile Tyr His Ile Asp Asn Ile Val Lys Pro Val Ser Lys Ala Gly
                340                 345                 350

His Ala Thr Lys Val Ile Phe Leu Thr Ala Asp Ala Phe Gly Val Leu
                355                 360                 365

Pro Pro Val Ser Arg Leu Thr Ala Asp Gln Thr Gln Tyr His Phe Leu
370                 375                 380

Ser Gly Phe Thr Ala Lys Leu Ala Gly Thr Glu Arg Gly Ile Thr Glu
385                 390                 395                 400

Pro Thr Pro Thr Phe Ser Ala Cys Phe Gly Ala Ala Phe Leu Ser Leu
                405                 410                 415

His Pro Thr Gln Tyr Ala Glu Val Leu Val Lys Arg Met Gln Ala Ala
                420                 425                 430

Gly Ala Gln Ala Tyr Leu Val Asn Thr Gly Trp Asn Gly Thr Gly Lys
                435                 440                 445

Arg Ile Ser Ile Lys Asp Thr Arg Ala Ile Ile Asp Ala Ile Leu Asn
450                 455                 460

Gly Ser Leu Asp Asn Ala Glu Thr Phe Thr Leu Pro Met Phe Asn Leu
465                 470                 475                 480

Ala Ile Pro Thr Glu Leu Pro Gly Val Asp Thr Lys Ile Leu Asp Pro
                485                 490                 495

Arg Asn Thr Tyr Ala Ser Pro Glu Gln Trp Gln Glu Lys Ala Glu Thr
                500                 505                 510

Leu Ala Lys Leu Phe Ile Asp Asn Phe Asp Lys Tyr Thr Asp Thr Pro
                515                 520                 525

Ala Gly Ala Ala Leu Val Ala Ala Gly Pro Lys Leu
530                 535                 540

<210> SEQ ID NO 24
<211> LENGTH: 811
<212> TYPE: DNA
<213> ORGANISM: Escherichia coli

<400> SEQUENCE: 24
tctgacgcat aatgacgtcg cattaatgat cgcaacctat ttattacaac agggcaaatc    60
ttgacggcta gctcagtcct aggtacagtg ctagctaagt aggtacgtaa ggaggtgata   120
aatggcgaga cgtattctgg tcgtagaaga tgaagctcca attcgcgaaa tggtctgctt   180
cgtgctcgaa caaaatggct ttcagccggt cgaagcggaa gattatgaca gtgctgtgaa   240

```
tcaactgaat gaaccctggc cggatttaat tctcctcgac tggatgttac ctggcggctc      300
cggtatccag ttcatcaaac acctcaagcg cgagtcgatg acccgggata ttccagtggt      360
gatgttgacc gccagagggg aagaagaaga tcgcgtgcgc ggccttgaaa ccggcgcgga      420
tgactatatc accaagccgt tttcgccgaa ggagctggtg gcgcgaatca aagcggtaat      480
gcgccgtatt tcgccaatgg cggtggaaga ggtgattgag atgcagggat taagtctcga      540
cccgacatct caccgagtga tggcgggcga agagccgctg gagatggggc cgacagaatt      600
taaactgctg cacttttttta tgacgcatcc tgagcgcgtg tacagccgcg agcagctgtt      660
aaaccacgtc tggggaacta acgtgtatgt ggaagaccgc acggtcgatg tccacattcg      720
tcgcctgcgt aaagcactgg agcccggcgg gcatgaccgc atggtgcaga ccgtgcgcgg      780
tacaggatat cgttttttcaa cccgctttta a                                   811

<210> SEQ ID NO 25
<211> LENGTH: 1159
<212> TYPE: DNA
<213> ORGANISM: Escherichia coli

<400> SEQUENCE: 25
ctgttagaat tgcgccgaat tttatttttc taccgcaagt aacgcgtggg gacccaagca       60
ttgacggcta gctcagtcct aggtacagtg ctagctaagt aggtacgtaa ggaggtgata      120
agtgaccgat aaaacctctc ttagctacaa agatgccggt gttgatattg acgcgggtaa      180
tgctctggtt ggaagaatca aaggcgtagt gaagaaaacg cgtcgtccgg aagtgatggg      240
cggtctgggc ggcttcggtg cgctgtgtgc attgccgcaa aaatatcgtg aacccgtgct      300
ggtttctggc actgacggcg taggtaccaa gctgcgtctg gcaatggact aaaaacgtca      360
cgacaccatt ggtattgatc tggtcgccat gtgcgttaat gacctggtgg tgcaaggtgc      420
agagccgctg tttttcctcg actattacgc aaccggaaaa ctggatgttg ataccgcttc      480
agcggtgatc agcggcattg cggaaggttg tctgcaatca ggctgttcac tggtgggtgg      540
cgaaacggca gaaatgccgg ggatgtatca cggtgaggat tacgatgtcg cgggtttctg      600
cgttggcgtg gtagaaaaat cagaaatcat cgacggctct aaagtcagcg acggcgatgt      660
gctgattgca ctcggttcca gcggtccaca ctcgaacggc tattcgctgg tgcgcaaaat      720
tcttgaagtc agcggttgtg atccgcaaac caccgaactt gatggtaagc cattagccga      780
tcatctgctg gcaccgaccc gcatttacgt gaagtcagtg ctggagttga ttgaaaaggt      840
cgatgtgcat gccattgcgc acctgaccgg cggcggcttc tgggaaaaca ttccgcgcgt      900
attgccagat aatactcagg cagtgattga tgaatcttcc tggcagtggc cggaagtgtt      960
caactggctg caaacggcag gtaacgttga gcaccatgaa atgtatcgca ccttcaactg     1020
cggcgtcggg atgattattg ccctgcctgc tccggaagtg acaaagccc tcgccctgct     1080 caatgccaac ggtgaaaacg cgtggaaaat cggtatcatc aaagcctctg attccgaaca     1140
acgcgtggtt atcgaataa                                                 1159

<210> SEQ ID NO 26
<211> LENGTH: 4
<212> TYPE: PRT
<213> ORGANISM: Escherichia coli

<400> SEQUENCE: 26

Met Asn Ser Leu
1
```

<210> SEQ ID NO 27
<211> LENGTH: 4
<212> TYPE: PRT
<213> ORGANISM: Escherichia coli

<400> SEQUENCE: 27

Met Asn Thr Asn
1

<210> SEQ ID NO 28
<211> LENGTH: 703
<212> TYPE: DNA
<213> ORGANISM: Escherichia coli

<400> SEQUENCE: 28

```
ctgttgtcgc ctgctctgga ttaacggata ataggcggct tttttatttc aggccgaaaa    60
ttgacggcta gctcagtcct aggtacagtg ctagctaagt aggtacgtaa ggaggtgata   120
aatgactgac tacctgttac tgtttgtcgg aactgtactg gtcaataact ttgtactggt   180
caagtttctc ggtctctgtc cgtttatggg ggtttccaaa aaactggaaa ccgcgatggg   240
catggggctg caacaacgtt tgtgatgac gctggcgtct atttgcgcct ggcttatcga   300
tacgtggatt tgatcccac ttaatctgat ttacctgcgc accctggcat ttattctggt   360
gattgctgtg tcgtgcagt tcaccgagat ggtggtgcg aaaaccagcc cggtgcttta   420
ccgtctgctg gggattttt tgccgcttat caccaccaac tgtgcagtgc tcggcgtggc   480
gttgctgaat atcaatctcg gcacaaattt cttgcagtcg cgctgtacg ttttttccgc   540 cgctgtcggt ttctcgctgg tgatggtgct cttcgccgcc atccgcgaac gccttgctgt   600
ggctgatgtc ccggcacctt tcgcggtaa tgccattgcg ttaattaccg caggtcttat   660
gtctctggcc tttatgggct ttagtggttt ggtgaagttg taa                     703
```

<210> SEQ ID NO 29
<211> LENGTH: 1480
<212> TYPE: DNA
<213> ORGANISM: Escherichia coli

<400> SEQUENCE: 29

```
aaagatgcgg caagtgaatt tgccgcaatt gctacctttt tagcaaatcc gaggcaccta    60
ttgacggcta gctcagtcct aggtacagtg ctagctaagt aggtacgtaa ggaggtgata   120
aatggaacaa tatgatcaaa ttggcgcaag actggaccgc ttgcctttgg cccggtttca   180
ttatcgtata tttggtatta taagctttag tctgttatta acagggtttt tgagttactc   240
cggtaatgtc gtcttagcaa agctggtaag caatggatgg tcaaataatt tcctcaatgc   300
cgcctttacc tcggcattaa tgtttggtta tttcatcggc tcacttactg gtgggtttat   360
tggtgactac tttgggcggc cagggcgtt tcgcataaat cttctcatcg tcggtattgc   420
tgcaacaggg gccgcttttg tccctgatat gtactggctc atcttctttc gcttcctgat   480
gggaacagga atgggggcgc tgattatggt tggctatgcc tcatttacgg agtttatccc   540
cgcgacggtg cgtggaaaat ggtccgcgcg gctctcattt gttggtaact ggtcgcccat   600
gctgtctgcg gcgataggcg tggtggttat cgctttttt agttggcgaa taatgtttct   660
gctgggtggt attggcatac tgttagcctg gtttctctca ggtaaatact ttatcgagtc   720
gccacgatgg ctggcaggga aagggcaaat cgcaggtgca gaatgccaac ttcgtgaagt   780
agagcagcaa attgaaagag agaagagtat tcgtttaccc ccgcttactt cgtatcagag   840
```

```
caacagcaag gttaaagtaa tcaagggtac tttctggctc ctgtttaaag gtgaaatgtt      900
acgacgtaca ttagtcgcga ttactgtttt aattgcaatg aacatttcgc tttataccat      960
caccgtatgg ataccgacca tatttgttaa ctccggcatt gatgtcgata aatcaatatt     1020
aatgaccgct gttattatga ttggcgctcc ggtaggaata tttattgcgg cattaattat     1080
tgatcatttt cctcgtcggt tatttggctc caccttactt attattattg ccgtgttagg     1140
ctatatctat tcaattcaga ctacagagtg ggcgatttta atctatggac tggtgatgat     1200
cttcttttta tacatgtatg tttgcttcgc gtcggcggtt tatatcccgg agctttggcc     1260
aacgcattta cgcctgcgcg gttcgggttt cgttaatgcc gtcggacgga tcgtcgcagt     1320
cttcacgccc tatggcgttg cggcattatt aacacattat gggtcgatca cggtgtttat     1380
ggtacttggt gttatgttat tgctctgtgc gctggttctc tccattttg gcatcgaaac     1440 gcggaaggtg tcgttggaag agatttctga ggtgaattaa                           1480

<210> SEQ ID NO 30
<211> LENGTH: 1045
<212> TYPE: DNA
<213> ORGANISM: Escherichia coli

<400> SEQUENCE: 30
tcgccatttt tgctatcatg cctgcataca taaacgacaa acagtatgc agagggaaaa       60 ttgacggcta gctcagtcct aggtacagtg ctagctaagt aggtacgtaa ggaggtgata     120
aatgggttcc accagaaagg ggatgctgaa cgttctgatt gccgccgtgt tgtggggaag     180
ttcagggctc tgcgcgcaat acatcatgga gcaaagccag atgtcgtcgc agttttgac     240 tatgacgcgt ttgatattcg ccggtttgat tctactgacg ctgtcatttg ttcatggcga     300
taaaatcttt tctattatta acaatcataa agatgccatt agcctgctga ttttttccgt     360
ggttggcgcg ctaactgtac agctcacttt tttgctaacc atcgaaaaat cgaacgcagc     420
cacggcaacg gtgctgcaat tcctctcacc gacgattatc gtcgcctggt tctcactggt     480
gcgtaaatcg cgcccgggca ttctggtttt ctgcgctatt ttgacatcgc tggtcgggac     540
ttttttattg gtgacacacg gtaatccgac gtcattatcg atctctcctg ccgcgttgtt     600
ctggggcatt gcctcggcat tgctgctgc attctatacc acctatccct caacgctaat     660
tgcccgctat ggcacgttac cagtcgtcgg ctggagtatg ctgattggcg gtctgattct     720
gttgcctttt tatgccagac aaggaacaaa cttttgtcgtt aacggcagtt tgattctggc     780
gtttttttat ttggtggtca ttggtacgtc cctgacattt agtctgtacc tgaaaggagc     840
acaattaatt ggcggtccaa aagccagcat tttgagctgt gcagaaccat taagtagcgc     900
gctactctct ttgctgttgc tggggatcac gttcacatta ccggactggc tgggaacgct     960
gctgattctg tcatcggtga ttttgatttc aatggattcc cgtcgccgcg ccagaaaaat    1020
aaatcgtccg gcgcggcata agtga                                          1045

<210> SEQ ID NO 31
<211> LENGTH: 2470
<212> TYPE: DNA
<213> ORGANISM: Escherichia coli

<400> SEQUENCE: 31
caagggacaa ttttttgcagc ggcacagcgt tcagatagtt attttgttaa atgtattaac       60
ttgacggcta gctcagtcct aggtacagtg ctagctaagt aggtacgtaa ggaggtgata     120
```

```
aatgctgagt ttatacgaaa agataaagat aaggctgata attttatttt tattggcagc      180
actgtcattt attggtcttt ttttcatcat taactatcaa ctggtatcgg agcgcgcggt      240
aaaacgtgcc gatagccgct ttgaacttat tcagaaaaac gttggctatt tctttaaaga      300
tattgaacgt tcggccctga cattaaagga ctcactgtat ttattaaaaa atacagagga      360
gattcaacgc gccgtgattc ttaaaatgga aatgatgcca tttttagact cggtgggact      420
ggtacttgat gataataaat attatctttt ttcgcggagg gcgaatgata aaatcgttgt      480
ttatcatcag gaacaagtaa atggaccgct tgtcgacgag tcagggcggg ttattttttgc     540 cgatttttaac ccatcgaaac gaccgtggtc ggtggcttca gatgactcta acaacagctg    600
gaatccggca tacaattgct tgatcgtccc gggtaaaaaa tgtatctctt ttacgctaca     660
catcaacggc aaagatcacg atttgttagc ggtggataaa attcatgtcg atttaaactg    720
gcgatatctg aacgagtatc ttgatcaaat cagcgctaat gatgaagttc tatttttgaa    780
acaaggccat gagatcattg ccaagaatca actcgctcgt gaaaaactga ttatttataa    840
tagcgaaggt aattataata ttattgattc tgtcgatact gaatatatcg aaaaaacatc    900
agcggtgcca acaacgcat tattcgaaat ctatttttat tatcctggcg gtaatttatt    960
gaacgcatca gataaacttt tttatctgcc gtttgcgttc attattatcg tattgctggt   1020
ggtttattta atgaccactc gtgtgttccg tcggcaattt tctgaaatga cagagctggt   1080
taatacgctg gcgttttgc ctgactcaac ggatcaaatc gaggctctga aaattcgtga    1140
aggcgatgcg aaagagatta tcagcatcaa aaattcgatc gcggaaatga agatgccga   1200 aattgaacgg tcaaataaat tgctctcact gatctcttac gatcaggaaa gtggtttat    1260 taaaaatatg gcgattattg agtctaacaa taatcagtat ctggctgtgg ggatcatcaa   1320
actgtgtggt ctggaagccg tggaagcggt gtttggtgtt gatgagcgca ataaaatcgt   1380
caggaaattg tgtcagcgaa ttgccgagaa atatgcgcaa tgctgcgata tcgtgacatt   1440
caatgccgat ctctatttac ttctgtgtcg ggaaaatgta cagacattta cccgtaaaat   1500
agcgatggta acgattttg acagcagctt tggctaccgc aatctgcgca tccataagtc    1560
tgccatttgt gaacctttgc aggggaaaa cgcctggagt tacgcagaaa aactgaaact   1620
ggcgatttcc agtatccgtg accatatgtt ctcagagttt attttctgtg atgacgcgaa   1680
actcaacgaa atagaagaga atatctggat tgcgcgtaat attcgccatg caatggaaat   1740
tggcgaacta ttcctcgtct atcaaccgat cgttgatatt aacacccgcg ccattctggg   1800
cgcggaggcg ttgtgccgtt gggtgtctgc ggagcggggg atcatttcac cgctgaagtt    1860
cattaccatt gctgaagata tcgggtttat caatgagctg ggttatcaga ttattaaaac   1920
ggcaatgggt gaattcagac attttagtca gcgtgcgtcg ctgaaggatg atttcttact   1980
gcatattaat gtttcgccct ggcagttaaa cgaaccacac tttcatgagc gttttaccac   2040
catcatgaaa gaaaatggcc tgaaggcgaa cagcctctgt gttgagatca ctgaaaccgt   2100
gatcgagcga attaatgaac attttttatct caatattgaa caactgcgta acaaggggt    2160 acggatatcg attgatgact ttggcaccgg tttgtcaaac ctgaaacgtt tttatgaaat   2220
taatccagac agcataaagg tggactcgca attcaccggc gatattttcg gtactgcggg   2280
aaaaattgtg cgcattattt tcgacctggc acgctataac cggatcccgg tgattgcgga   2340
aggcgtagag agcgaagacg ttgcgcgcga attaatcaaa ttaggatgtg ttcaggctca   2400
ggggtatctg taccagaaac ccatgccatt ctccgcctgg gataaaagtg gaaaattagt   2460
aaaagagtag                                                            2470
```

<210> SEQ ID NO 32
<211> LENGTH: 883
<212> TYPE: DNA
<213> ORGANISM: Escherichia coli

<400> SEQUENCE: 32

```
aacgctgatg atatgcgcct tctatactta acgtttattc agcgttaagt ggagaactcg    60
ttgacggcta gctcagtcct aggtacagtg ctagctaagt aggtacgtaa ggaggtgata   120
aatggcacag gttgcgatta ttaccgcctc cgattcgggg atcggcaaag agtgcgcgtt   180
attactggcg cagcagggt ttgatattgg tattacctgg cactcagatg aagaaggggc    240
aaaagatacc gcgcgtgagg tagttagcca cggcgtacgt gcggagatcg tgcagctgga   300
tctcggcaat ctaccagaag gggcactggc gctggagaaa ctcattcaac ggctggggcg   360
cattgatgtg ctggtgaata atgcgggtgc aatgaccaaa gcgccgtttc ttgatatggc   420
ttttgatgag tggcgcaaga ttttttaccgt tgatgtcgat ggtgcattct tatgctcgca   480
aattgcggct cgtcagatgg tgaaacaagg gcagggcggt cgcatcatca acattacgtc   540
ggtacatgaa catacgccgc tgccggatgc cagcgcctac acagccgcta acatgcgct    600
cggtgggtta accaaagcga tggcgctgga gctggtcagg cataagattt tggtgaacgc   660
agtcgcgcct ggggcgatcg ccacgccaat gaatggcatg gatgacagcg acgtgaagcc   720
cgacgcggag ccttcgattc ccttgcggcg ttttggcgca acgcatgaga ttgccagcct   780
ggtggtgtgg ctttgttcgg agggcgcaaa ttacaccacc gggcagtcgt tgatagtgga   840
tggcggcttt atgttggcga atccacagtt caacccagaa tag                    883
```

<210> SEQ ID NO 33
<211> LENGTH: 14
<212> TYPE: PRT
<213> ORGANISM: Escherichia coli

<400> SEQUENCE: 33

Met Arg Ile Phe Val Tyr Gly Ser Leu Arg His Lys Gln Gly
1               5                   10

<210> SEQ ID NO 34
<211> LENGTH: 93
<212> TYPE: PRT
<213> ORGANISM: Escherichia coli

<400> SEQUENCE: 34

Met Ser Arg Arg Asn Thr Asp Ala Ile Thr Ile His Ser Ile Leu Asp
1               5                   10                  15

Trp Ile Glu Asp Asn Leu Glu Ser Pro Leu Ser Leu Glu Lys Val Ser
                20                  25                  30

Glu Arg Ser Gly Tyr Ser Lys Trp His Leu Gln Arg Met Phe Lys Lys
            35                  40                  45

Glu Thr Gly His Ser Leu Gly Gln Tyr Ile Arg Ser Arg Lys Met Thr
        50                  55                  60

Glu Ile Ala Gln Lys Leu Lys Glu Ser Asn Glu Pro Ile Leu Tyr Leu
65                  70                  75                  80

Ala Glu Arg Tyr Gly Phe Glu Ser Gln Gln Thr Leu Thr
                85                  90

<210> SEQ ID NO 35
<211> LENGTH: 127

```
<212> TYPE: PRT
<213> ORGANISM: Escherichia coli

<400> SEQUENCE: 35

Met Ser Arg Arg Asn Thr Asp Ala Ile Thr Ile His Ser Ile Leu Asp
1               5                   10                  15

Trp Ile Glu Asp Asn Leu Glu Ser Pro Leu Ser Leu Glu Lys Val Ser
                20                  25                  30

Glu Arg Ser Gly Tyr Ser Lys Trp His Leu Gln Arg Met Phe Lys Lys
            35                  40                  45

Glu Thr Gly His Ser Leu Gly Gln Tyr Ile Arg Ser Arg Lys Met Thr
        50                  55                  60

Glu Ile Ala Gln Lys Leu Lys Glu Ser Asn Glu Pro Ile Leu Tyr Leu
65                  70                  75                  80

Ala Glu Arg Tyr Gly Phe Glu Ser Gln Gln Thr Leu Thr Arg Thr Phe
                85                  90                  95

Lys Asn Tyr Phe Asp Val Pro Pro His Lys Lys Arg Met Thr Asn Met
                100                 105                 110

Gln Gly Glu Ser Arg Phe Leu His Pro Leu Asn His Tyr Asn Ser
            115                 120                 125

<210> SEQ ID NO 36
<211> LENGTH: 810
<212> TYPE: PRT
<213> ORGANISM: Escherichia coli

<400> SEQUENCE: 36

Met Ser Val Ile Ala Gln Ala Gly Ala Lys Gly Arg Gln Leu His Lys
1               5                   10                  15

Phe Gly Gly Ser Ser Leu Ala Asp Val Lys Cys Tyr Leu Arg Val Ala
                20                  25                  30

Gly Ile Met Ala Glu Tyr Ser Gln Pro Asp Asp Met Met Val Val Ser
            35                  40                  45

Ala Ala Gly Ser Thr Thr Asn Gln Leu Ile Asn Trp Leu Lys Leu Ser
        50                  55                  60

Gln Thr Asp Arg Leu Ser Ala His Gln Val Gln Gln Thr Leu Arg Arg
65                  70                  75                  80

Tyr Gln Cys Asp Leu Ile Ser Gly Leu Leu Pro Ala Glu Glu Ala Asp
                85                  90                  95

Ser Leu Ile Ser Ala Phe Val Ser Asp Leu Glu Arg Leu Ala Ala Leu
                100                 105                 110

Leu Asp Ser Gly Ile Asn Asp Ala Val Tyr Ala Glu Val Val Gly His
            115                 120                 125

Gly Glu Val Trp Ser Ala Arg Leu Met Ser Ala Val Leu Asn Gln Gln
        130                 135                 140

Gly Leu Pro Ala Ala Trp Leu Asp Ala Arg Glu Phe Leu Arg Ala Glu
145                 150                 155                 160

Arg Ala Ala Gln Pro Gln Val Asp Glu Gly Leu Ser Tyr Pro Leu Leu
                165                 170                 175

Gln Gln Leu Leu Val Gln His Pro Gly Lys Arg Leu Val Val Thr Gly
                180                 185                 190

Phe Ile Ser Arg Asn Asn Ala Gly Glu Thr Val Leu Leu Gly Arg Asn
            195                 200                 205

Gly Ser Asp Tyr Ser Ala Thr Gln Ile Gly Ala Leu Ala Gly Val Ser
        210                 215                 220
```

-continued

```
Arg Val Thr Ile Trp Ser Asp Val Ala Gly Val Tyr Ser Ala Asp Asp
225                 230                 235                 240

Arg Lys Val Lys Asp Ala Cys Leu Leu Pro Leu Leu Arg Leu Asp Glu
            245                 250                 255

Ala Ser Glu Leu Ala Arg Leu Ala Ala Pro Val Leu His Ala Arg Thr
        260                 265                 270

Leu Gln Pro Val Ser Gly Ser Glu Ile Asp Leu Gln Leu Arg Cys Ser
    275                 280                 285

Tyr Thr Pro Asp Gln Gly Ser Thr Arg Ile Glu Arg Val Leu Ala Ser
290                 295                 300

Gly Thr Gly Ala Arg Ile Val Thr Ser His Asp Asp Val Cys Leu Ile
305                 310                 315                 320

Glu Phe Gln Val Pro Ala Ser Gln Asp Phe Lys Leu Ala His Lys Glu
                325                 330                 335

Ile Asp Gln Ile Leu Lys Arg Ala Gln Val Arg Pro Leu Ala Val Gly
            340                 345                 350

Val His Asn Asp Arg Gln Leu Leu Gln Phe Cys Tyr Thr Ser Glu Val
        355                 360                 365

Ala Asp Ser Ala Leu Lys Ile Leu Asp Glu Ala Gly Leu Pro Gly Glu
    370                 375                 380

Leu Arg Leu Arg Gln Gly Leu Ala Leu Val Ala Met Val Gly Ala Gly
385                 390                 395                 400

Val Thr Arg Asn Pro Leu His Cys His Arg Phe Trp Gln Gln Leu Lys
                405                 410                 415

Gly Gln Pro Val Glu Phe Thr Trp Gln Ser Asp Asp Gly Ile Ser Leu
            420                 425                 430

Val Ala Val Leu Arg Thr Gly Pro Thr Glu Ser Leu Ile Gln Gly Leu
        435                 440                 445

His Gln Ser Val Phe Arg Ala Glu Lys Arg Ile Gly Leu Val Leu Phe
    450                 455                 460

Gly Lys Gly Asn Ile Gly Ser Arg Trp Leu Glu Leu Phe Ala Arg Glu
465                 470                 475                 480

Gln Ser Thr Leu Ser Ala Arg Thr Gly Phe Glu Phe Val Leu Ala Gly
                485                 490                 495

Val Val Asp Ser Arg Arg Ser Leu Leu Ser Tyr Asp Gly Leu Asp Ala
            500                 505                 510

Ser Arg Ala Leu Ala Phe Phe Asn Asp Glu Ala Val Glu Gln Asp Glu
        515                 520                 525

Glu Ser Leu Phe Leu Trp Met Arg Ala His Pro Tyr Asp Asp Leu Val
    530                 535                 540

Val Leu Asp Val Thr Ala Ser Gln Gln Leu Ala Asp Gln Tyr Leu Asp
545                 550                 555                 560

Phe Ala Ser His Gly Phe His Val Ile Ser Ala Asn Lys Leu Ala Gly
                565                 570                 575

Ala Ser Asp Ser Asn Lys Tyr Arg Gln Ile His Asp Ala Phe Glu Lys
            580                 585                 590

Thr Gly Arg His Trp Leu Tyr Asn Ala Thr Val Gly Ala Gly Leu Pro
        595                 600                 605

Ile Asn His Thr Val Arg Asp Leu Ile Asp Ser Gly Asp Thr Ile Leu
    610                 615                 620

Ser Ile Ser Gly Ile Phe Ser Gly Thr Leu Ser Trp Leu Phe Leu Gln
625                 630                 635                 640

Phe Asp Gly Ser Val Pro Phe Thr Glu Leu Val Asp Gln Ala Trp Gln
```

```
                        645                 650                 655
Gln Gly Leu Thr Glu Pro Asp Pro Arg Asp Asp Leu Ser Gly Lys Asp
            660                 665                 670

Val Met Arg Lys Leu Val Ile Leu Ala Arg Glu Ala Gly Tyr Asn Ile
            675                 680                 685

Glu Pro Asp Gln Val Arg Val Glu Ser Leu Val Pro Ala His Cys Glu
            690                 695                 700

Gly Gly Ser Ile Asp His Phe Phe Glu Asn Gly Asp Glu Leu Asn Glu
705                 710                 715                 720

Gln Met Val Gln Arg Leu Glu Ala Ala Arg Glu Met Gly Leu Val Leu
                725                 730                 735

Arg Tyr Val Ala Arg Phe Asp Ala Asn Gly Lys Ala Arg Val Gly Val
                740                 745                 750

Glu Ala Val Arg Glu Asp His Pro Leu Ala Ser Leu Leu Pro Cys Asp
                755                 760                 765

Asn Val Phe Ala Ile Glu Ser Arg Trp Tyr Arg Asp Asn Pro Leu Val
                770                 775                 780

Ile Arg Gly Pro Gly Ala Gly Arg Asp Val Thr Ala Gly Ala Ile Gln
785                 790                 795                 800

Ser Asp Ile Asn Arg Leu Ala Gln Leu Leu
                805                 810

<210> SEQ ID NO 37
<211> LENGTH: 810
<212> TYPE: PRT
<213> ORGANISM: Escherichia coli

<400> SEQUENCE: 37

Met Ser Val Ile Ala Gln Ala Gly Ala Lys Gly Arg Gln Leu His Lys
1               5                   10                  15

Phe Gly Gly Ser Ser Leu Ala Asp Val Lys Cys Tyr Leu Arg Val Ala
                20                  25                  30

Gly Ile Met Ala Glu Tyr Ser Gln Pro Asp Asp Met Met Val Val Ser
            35                  40                  45

Ala Ala Gly Ser Thr Thr Asn Gln Leu Ile Asn Trp Leu Lys Leu Ser
    50                  55                  60

Gln Thr Asp Arg Leu Ser Ala His Gln Val Gln Gln Thr Leu Arg Arg
65                  70                  75                  80

Tyr Gln Cys Asp Leu Ile Ser Gly Leu Leu Pro Ala Glu Glu Ala Asp
                85                  90                  95

Ser Leu Ile Ser Ala Phe Val Ser Asp Leu Glu Arg Leu Ala Ala Leu
                100                 105                 110

Leu Asp Ser Gly Ile Asn Asp Ala Val Tyr Ala Glu Val Val Gly His
            115                 120                 125

Gly Glu Val Trp Ser Ala Arg Leu Met Ser Ala Val Leu Asn Gln Gln
    130                 135                 140

Gly Leu Pro Ala Ala Trp Leu Asp Ala Arg Glu Phe Leu Arg Ala Glu
145                 150                 155                 160

Arg Ala Ala Gln Pro Gln Val Asp Glu Gly Leu Ser Tyr Pro Leu Leu
                165                 170                 175

Gln Gln Leu Leu Val Gln His Pro Gly Lys Arg Leu Val Val Thr Gly
                180                 185                 190

Phe Ile Ser Arg Asn Asn Ala Gly Glu Thr Val Leu Leu Gly Arg Asn
            195                 200                 205
```

```
Gly Ser Asp Tyr Ser Ala Thr Gln Ile Gly Ala Leu Ala Gly Val Ser
    210                 215                 220

Arg Val Thr Ile Trp Ser Asp Val Ala Gly Cys Tyr Ser Ala Asp Pro
225                 230                 235                 240

Arg Lys Val Lys Asp Ala Cys Leu Leu Pro Leu Leu Arg Leu Asp Glu
                245                 250                 255

Ala Ser Glu Leu Ala Arg Leu Ala Ala Pro Val Leu His Ala Arg Thr
            260                 265                 270

Leu Gln Pro Val Ser Gly Ser Glu Ile Asp Leu Gln Leu Arg Cys Ser
        275                 280                 285

Tyr Thr Pro Asp Gln Gly Ser Thr Arg Ile Glu Arg Val Leu Ala Ser
290                 295                 300

Gly Thr Gly Ala Arg Ile Val Thr Ser His Asp Asp Val Cys Leu Ile
305                 310                 315                 320

Glu Phe Gln Val Pro Ala Ser Gln Asp Phe Lys Leu Ala His Lys Glu
                325                 330                 335

Ile Asp Gln Ile Leu Lys Arg Ala Gln Val Arg Pro Leu Ala Val Gly
            340                 345                 350

Val His Asn Asp Arg Gln Leu Leu Gln Phe Cys Tyr Thr Ser Glu Val
        355                 360                 365

Ala Asp Ser Ala Leu Lys Ile Leu Asp Glu Ala Gly Leu Pro Gly Glu
370                 375                 380

Leu Arg Leu Arg Gln Gly Leu Ala Leu Val Ala Met Val Gly Ala Gly
385                 390                 395                 400

Val Thr Arg Asn Pro Leu His Cys His Arg Phe Trp Gln Gln Leu Lys
                405                 410                 415

Gly Gln Pro Val Glu Phe Thr Trp Gln Ser Asp Asp Gly Ile Ser Leu
            420                 425                 430

Val Ala Val Leu Arg Thr Gly Pro Thr Glu Ser Leu Ile Gln Gly Leu
        435                 440                 445

His Gln Ser Val Phe Arg Ala Glu Lys Arg Ile Gly Leu Val Leu Phe
450                 455                 460

Gly Lys Gly Asn Ile Gly Ser Arg Trp Leu Glu Leu Phe Ala Arg Glu
465                 470                 475                 480

Gln Ser Thr Leu Ser Ala Arg Thr Gly Phe Glu Phe Val Leu Ala Gly
                485                 490                 495

Val Val Asp Ser Arg Arg Ser Leu Leu Ser Tyr Asp Gly Leu Asp Ala
            500                 505                 510

Ser Arg Ala Leu Ala Phe Phe Asn Asp Glu Ala Val Glu Gln Asp Glu
        515                 520                 525

Glu Ser Leu Phe Leu Trp Met Arg Ala His Pro Tyr Asp Asp Leu Val
530                 535                 540

Val Leu Asp Val Thr Ala Ser Gln Gln Leu Ala Asp Gln Tyr Leu Asp
545                 550                 555                 560

Phe Ala Ser His Gly Phe His Val Ile Ser Ala Asn Lys Leu Ala Gly
                565                 570                 575

Ala Ser Asp Ser Asn Lys Tyr Arg Gln Ile His Asp Ala Phe Glu Lys
            580                 585                 590

Thr Gly Arg His Trp Leu Tyr Asn Ala Thr Val Gly Ala Gly Leu Pro
        595                 600                 605

Ile Asn His Thr Val Arg Asp Leu Ile Asp Ser Gly Asp Thr Ile Leu
610                 615                 620

Ser Ile Ser Gly Ile Phe Ser Gly Thr Leu Ser Trp Leu Phe Leu Gln
```

```
            625                 630                 635                 640
        Phe Asp Gly Ser Val Pro Phe Thr Glu Leu Val Asp Gln Ala Trp Gln
                        645                 650                 655

Gln Gly Leu Thr Glu Pro Asp Pro Arg Asp Asp Leu Ser Gly Lys Asp
                        660                 665                 670

Val Met Arg Lys Leu Val Ile Leu Ala Arg Glu Ala Gly Tyr Asn Ile
                        675                 680                 685

Glu Pro Asp Gln Val Arg Val Glu Ser Leu Val Pro Ala His Cys Glu
                        690                 695                 700

Gly Gly Ser Ile Asp His Phe Phe Glu Asn Gly Asp Glu Leu Asn Glu
        705                 710                 715                 720

Gln Met Val Gln Arg Leu Glu Ala Ala Arg Glu Met Gly Leu Val Leu
                        725                 730                 735

Arg Tyr Val Ala Arg Phe Asp Ala Asn Gly Lys Ala Arg Val Gly Val
                        740                 745                 750

Glu Ala Val Arg Glu Asp His Pro Leu Ala Ser Leu Leu Pro Cys Asp
                        755                 760                 765

Asn Val Phe Ala Ile Glu Ser Arg Trp Tyr Arg Asp Asn Pro Leu Val
                        770                 775                 780

Ile Arg Gly Pro Gly Ala Gly Arg Asp Val Thr Ala Gly Ala Ile Gln
        785                 790                 795                 800

Ser Asp Ile Asn Arg Leu Ala Gln Leu Leu
                        805                 810

<210> SEQ ID NO 38
<211> LENGTH: 540
<212> TYPE: PRT
<213> ORGANISM: Escherichia coli

<400> SEQUENCE: 38

Met Arg Val Asn Asn Gly Leu Thr Pro Gln Glu Leu Glu Ala Tyr Gly
        1               5                   10                  15

Ile Ser Asp Val His Asp Ile Val Tyr Asn Pro Ser Tyr Asp Leu Leu
                        20                  25                  30

Tyr Gln Glu Glu Leu Asp Pro Ser Leu Thr Gly Tyr Glu Arg Gly Val
                        35                  40                  45

Leu Thr Asn Leu Gly Ala Val Ala Val Asp Thr Gly Ile Phe Thr Asp
                        50                  55                  60

Arg Ser Pro Lys Asp Lys Tyr Ile Val Arg Asp Asp Thr Thr Arg Asp
        65                  70                  75                  80

Thr Phe Trp Trp Ala Asp Lys Gly Lys Gly Lys Asn Asp Asn Lys Pro
                        85                  90                  95

Leu Ser Pro Glu Thr Trp Gln His Leu Lys Gly Leu Val Thr Arg Gln
                        100                 105                 110

Leu Ser Gly Lys Arg Leu Phe Val Val Asp Ala Phe Cys Gly Ala Asn
                        115                 120                 125

Pro Asp Thr Arg Leu Ser Val Arg Phe Ile Thr Glu Val Ala Trp Gln
                        130                 135                 140

Ala His Phe Val Lys Asn Met Phe Ile Arg Pro Ser Asp Glu Glu Leu
        145                 150                 155                 160

Ala Gly Phe Lys Pro Asp Phe Ile Val Met Asn Gly Ala Lys Cys Thr
                        165                 170                 175

Asn Pro Gln Trp Lys Glu Gln Gly Leu Asn Ser Glu Asn Phe Val Ala
                        180                 185                 190
```

```
Phe Asn Leu Thr Glu Arg Met Gln Leu Ile Gly Gly Thr Trp Tyr Gly
            195                 200                 205
Gly Glu Met Lys Lys Gly Met Phe Ser Met Met Asn Tyr Leu Leu Pro
        210                 215                 220
Leu Lys Gly Ile Ala Ser Met His Cys Ser Ala Asn Val Gly Glu Lys
225                 230                 235                 240
Gly Asp Val Ala Val Phe Phe Gly Leu Ser Gly Thr Gly Lys Thr Thr
                245                 250                 255
Leu Ser Thr Asp Pro Lys Arg Arg Leu Ile Gly Asp Asp Glu His Gly
                260                 265                 270
Trp Asp Asp Asp Gly Val Phe Asn Phe Glu Gly Gly Cys Tyr Ala Lys
            275                 280                 285
Thr Ile Lys Leu Ser Lys Glu Ala Glu Pro Glu Ile Tyr Asn Ala Ile
        290                 295                 300
Arg Arg Asp Ala Leu Leu Glu Asn Val Thr Val Arg Glu Asp Gly Thr
305                 310                 315                 320
Ile Asp Phe Asp Asp Gly Ser Lys Thr Glu Asn Thr Arg Val Ser Tyr
                325                 330                 335
Pro Ile Tyr His Ile Asp Asn Ile Val Lys Pro Val Ser Lys Ala Gly
                340                 345                 350
His Ala Thr Lys Val Ile Phe Leu Thr Ala Asp Ala Phe Gly Val Leu
            355                 360                 365
Pro Pro Val Ser Arg Leu Thr Ala Asp Gln Thr Gln Tyr His Phe Leu
        370                 375                 380
Ser Gly Phe Thr Ala Lys Leu Ala Gly Thr Glu Arg Gly Ile Thr Glu
385                 390                 395                 400
Pro Thr Pro Thr Phe Ser Ala Cys Phe Gly Ala Ala Phe Leu Ser Leu
                405                 410                 415
His Pro Thr Gln Tyr Ala Glu Val Leu Val Lys Arg Met Gln Ala Ala
                420                 425                 430
Gly Ala Gln Ala Tyr Leu Val Asn Thr Gly Trp Asn Gly Thr Gly Lys
            435                 440                 445
Arg Ile Ser Ile Lys Asp Thr Arg Ala Ile Ile Asp Ala Ile Leu Asn
        450                 455                 460
Gly Ser Leu Asp Asn Ala Glu Thr Phe Thr Leu Pro Met Phe Asn Leu
465                 470                 475                 480
Ala Ile Pro Thr Glu Leu Pro Gly Val Asp Thr Lys Ile Leu Asp Pro
                485                 490                 495
Arg Asn Thr Tyr Ala Ser Pro Glu Gln Trp Gln Glu Lys Ala Glu Thr
                500                 505                 510
Leu Ala Lys Leu Phe Ile Asp Asn Phe Asp Lys Tyr Thr Asp Thr Pro
            515                 520                 525
Ala Gly Ala Ala Leu Val Ala Ala Gly Pro Lys Leu
        530                 535                 540

<210> SEQ ID NO 39
<211> LENGTH: 1303
<212> TYPE: DNA
<213> ORGANISM: Escherichia coli

<400> SEQUENCE: 39
tgtttatttt ctgacaagca gcgtaaactc cgcgtcttcc tcttccagtg atcgaccagc      60
ttgacggcta gctcagtcct aggtacagtg ctagctaagt aggtacgtaa ggaggtgata     120
aatgcataac tcccccgcag tctccagcgc gaaatcgttt gacctgacct cgacggcgtt     180
```

```
tttaatcgtt gcctttctca ccggtattgc gggcgctctg caaacccga cactcagtat    240 ttttcttacc gatgaagtac atgcccgtcc ggcgatggtg ggattcttct ttaccggcag    300
cgctgtcatt gggattctgg taagtcagtt tctcgccggg cgctctgata agcgcggcga    360
tcgcaaatcg ctgattgtct tttgctgcct gttaggcgtg ctggcctgca ccctttttgc    420
ctggaatcgc aactactttg ttttgctatt cgttggcgtc tttcttagca gctttggctc    480
gaccgctaac ccgcaaatgt tgcccttgc ccgtgaacat gccgacaaaa ccggacgtga    540
ggcggtgatg ttcagctctt ttttacgcgc tcaggtttca ctggcatggg tcattggccc    600
accgctggct tatgccttag cgatgggttt cagctttacg gtaatgtatc tgagcgcagc    660
ggtagcgttt attgtttgcg gtgtgatggt gtggctgttt ttaccgtcga tgcgaaaaga    720
gcttccgctg cgaccggca cgatcgaagc gccgcgccgt aaccgtcgcg atacgctgct    780
gctgtttgtc atttgtacat tgatgtgggg ctcgaacagc ctgtacatca tcaacatgcc    840
gctatttatt atcaacgaac tgcatcttcc cgagaaactg gccggtgtga tgatgggac    900 cgccgccggg ctggaaatcc cgacgatgtt gattgccgga tatttcgcca aacgtctggg    960
taagcgtttc ttaatgcgcg ttgctgccgt gggtggcgtc tgttttttacg caggaatgct    1020 gatggcgcat tcacctgtca ttctgttggg cttgcagctg ctaaatgcta ttttttattgg    1080 cattctgggc ggcatcggga tgctctattt tcaggatctg atgcccggtc aggcgggttc    1140
agccaccacg ctctatacca acacttcgcg cgtgggctgg atcatcgcag atcagtggc    1200 gggcatcgtc gccgagatct ggaattatca cgctgtgttc tggtttgcga tggtgatgat    1260
tatcgccact ctgttttgct tactgcggat taaagatgtt taa    1303
```

<210> SEQ ID NO 40
<211> LENGTH: 532
<212> TYPE: DNA
<213> ORGANISM: Escherichia coli

<400> SEQUENCE: 40

```
tgaagcaatt tagataatcg tgcagactac gcccctcat atcacatgga aggtttatct    60
ttgacggcta gctcagtcct aggtacagtg ctagctaagt aggtacgtaa ggaggtgata    120
aatggatcag gtagtcattt ttaaacaaat atttgataaa gttcgaaacg atttaaacta    180
tcaatggttt tattctgagc taaaacgtca caatgtctca cattacattt actatttagc    240
cacagagaat gttcatattg tattaaaaaa tgataataca gtgttattaa agggcctaaa    300
aaacattgtg tctgtcaaat tttcaaagga taggcatctt atagaaacga cctctaataa    360
gctgaaatcc agagagatca catttcagga atacagaaga aaccttgcta aagcaggagt    420
ttttcggtgg gttacaaata tccacgaaca aaaaagatat tactataccgt ttgataattc    480 attactattt actgaaagca tccagaaaac tacacagatc ttaccacgct aa    532
```

<210> SEQ ID NO 41
<211> LENGTH: 943
<212> TYPE: DNA
<213> ORGANISM: Escherichia coli

<400> SEQUENCE: 41

```
cgtctatagt atttatgagg gtttgctttt aataatcata attcccacc agagtgtgat    60 ttgacggcta gctcagtcct aggtacagtg ctagctaagt aggtacgtaa ggaggtgata    120
aatgcgtaca accattgctg tagtgttggg tgcaattagt ttgacgtctg cttttgtgtt    180
```

```
tgcagataaa ccagacgttg ccagatcggc aaacgatgag gtcagcaccc tgtttttttgg      240 tcatgatgat cgtgtgccag tgaatgacac gacccaatca ccgtgggatg cggttgggca      300
actggaaacg gccagcggca atttatgtac ggcgacgctg attgcaccca atctggcatt      360
aacggcagga cactgtttat tgacacctcc aaagggtaaa gccgataaag cagtggcgct      420
gcgttttgtg tcaaataaag gtctttggcg ctatgagatc cacgacatag aaggccgcgt      480
tgatccgaca ctgggaaagc ggttaaaagc agatggggat ggttggattg tacctcccgc      540
agccgcgccg tgggacttcg gattgattgt gctacgtaat ccccttctg gcattacgcc      600 gttgccgtta tttgagggag ataaagccgc gcttaccgcc gcattaaaag cggcaggtcg      660
taaagtgact caggcaggct accctgaaga tcatctcgat acgttgtaca gtcatcaaaa      720
ctgtgaagtg actggctggg cgcaaacgtc ggtgatgtca catcagtgcg ataccttgcc      780
gggtgacagc ggttcgcctc tgatgttgca taccgatgac ggctggcaat taattggggt      840
gcaaagttcg gctcctgccg cgaaagatcg ctggcgcgcc gataaccggg ccatttctgt      900
taccggtttt cgcgacaagc tggatcaact gtcgcaaaaa taa                       943

<210> SEQ ID NO 42
<211> LENGTH: 466
<212> TYPE: DNA
<213> ORGANISM: Escherichia coli

<400> SEQUENCE: 42
atgatgtgtt aaaattgatg taaacaaatt gtgaagtgaa tgtgcttccg gggaaaataa       60
ttgacggcta gctcagtcct aggtacagtg ctagctaagt aggtacgtaa ggaggtgata      120
agtgacttca ttacaactct caatcgtcca tcgactgccg cagaactatc gctggtctgc      180
tggtttcgca ggttcgaagg ttgaaccgat tccgcaaaat ggaccgtgcg gtgacaacag      240
cctggtggcg cttaaattgc ttagcccgga tggtgataat gcatggtcgg tgatgtataa      300
actaagccag gcgttaagcg acatcgaagt tccatgttcg gtgctggagt gtgaaggtga      360
gccgtgcctg tttgtaaatc gccaggacga gtttgctgca acatgccgat tgaaaaattt      420
tggtgtggca attgccgaac cctttcaaa ctacaatcct ttttaa                     466
```

GENOME-WIDE RATIONALLY-DESIGNED MUTATIONS LEADING TO ENHANCED LYSINE PRODUCTION IN E. COLI

RELATED APPLICATIONS

This application is a continuation of U.S. Ser. No. 16/904,827, filed 18 Jun. 2020, entitled "Genome-Wide Rationally-Designed Mutations Leading to Enhanced Lysine Production in *E. Coli*"; which claims priority to U.S. Provisional Applications No. 62/865,075, filed 21 Jun. 2019, entitled "Genome-Wide Rationally-Designed Mutations Leading to Enhanced Lysine Production in *E. Coli*", incorporated by reference herein in its entirety.

FIELD OF THE INVENTION

The present disclosure relates to mutations in genes in *E. coli* leading to enhanced lysine production.

INCORPORATION BY REFERENCE

Submitted with the present application is an electronically filed sequence listing via EFS-Web as an ASCII formatted sequence listing, entitled "INSC046US2_seglist", created Jan. 12, 2020, and 83,198 bytes in size. The sequence listing is part of the specification filed Jan. 26, 2021 and is incorporated by reference in its entirety.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The amino acid lysine is an α-amino acid that is used in the biosynthesis of proteins and is a metabolite of *E. coli, S. cerevisiae*, plants, humans and other mammals, as well as algae. Lysine contains an α-amino group, an α-carboxylic acid group, and has a chemical formula of $C_6H_{14}N_2O_2$ One of nine essential amino acids in humans, lysine is required for growth and tissue repair and has a role as a micronutrient, a nutraceutical, an agricultural feed supplement, an anticonvulsant, as well as a precursor for the production of peptides. Because of these roles as, e.g., a supplement and nutraceutical, there has been a growing effort to produce lysine on a large scale.

Accordingly, there is a need in the art for organisms that produce enhanced amounts of lysine where such organisms can be harnessed for large scale lysine production. The disclosed nucleic acid sequences from *E. coli* satisfy this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides variant *E. coli* genes and non-coding sequences that produce enhanced amounts of lysine in culture including double and triple combinations of variant sequences. Thus, in some embodiments, the present disclosure provides any one of SEQ ID Nos. 2-42.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 1B is a continuation of FIG. 1A.

FIG. 2 enumerates the biological target, edit outcome, edit type and scale for the initial 200,000 edits made to the *E. coli* lysine pathway.

It should be understood that the drawings are not necessarily to scale, and that like reference numbers refer to like features.

DETAILED DESCRIPTION

Figure 1A:
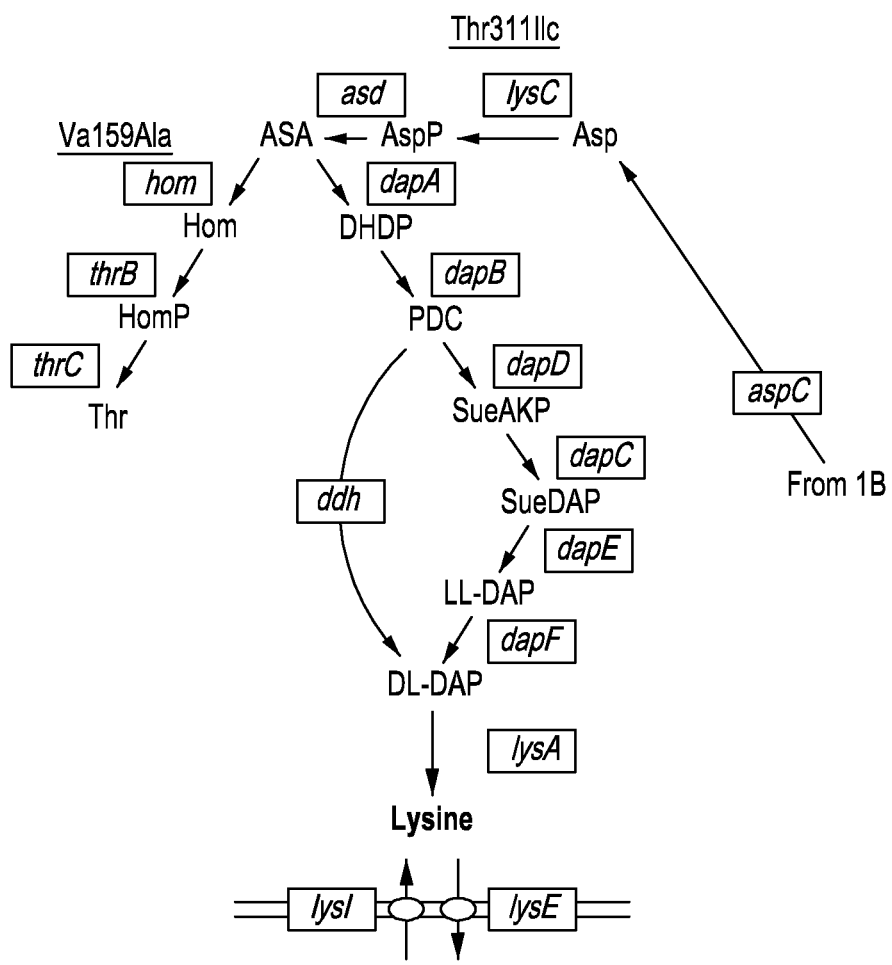
FIGS. 1A and 1B are graphic depictions of the lysine pathway in *E. coli*, highlighting the enzymes in the pathway targeted for rationally-designed editing.

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual.* 4th, ed., Cold Spring Harbor Laboratory Press, Cold Spring Harbor, N.Y., (2014); *Current Protocols in Molecular Biology*, Ausubel, et al. eds., (2017); Neumann, et al., *Electroporation and Electrofusion in Cell Biology*, Plenum Press, New York, 1989; and Chang, et al., *Guide to Electroporation and Electrofusion*, Academic Press, California (1992), all of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

The term "CREATE cassette" or "editing cassette" refers to a gRNA linked to a donor DNA or HA. Methods and compositions for designing and synthesizing CREATE editing cassettes are described in U.S. Pat. Nos. 10,240,167; 10,266,849; 9,982,278; 10,351,877; 10,364,442; 10,435,715; and 10,465,207; and U.S. Ser. Nos. 16/550,092, filed 23 Aug. 2019; 16/551,517, filed 26 Aug. 2019; 16/773,618, filed 27 Jan. 2020; and 16/773,712, filed 27 Jan. 2020, all of which are incorporated by reference herein in their entirety.

As used herein the term "donor DNA" or "donor nucleic acid" refers to nucleic acid that is designed to introduce a DNA sequence modification (insertion, deletion, substitution) into a locus (e.g., a target genomic DNA sequence or cellular target sequence) by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region— the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the genomic target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the genomic target sequence.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

As used herein, the terms "protein" and "polypeptide" are used interchangeably. Proteins may or may not be made up entirely of amino acids.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible, and in some embodiments the transcription of at least one component of the nucleic acid-guided nuclease editing system is—and often at least three components of the nucleic acid-guided nuclease editing system are—under the control of an inducible promoter. A number of gene regulation control systems have been developed for the controlled expression of genes in plant, microbe, and animal cells, including mammalian cells, including the pL promoter (induced by heat inactivation of the CI857 repressor), the pPhIF promoter (induced by the addition of 2,4 diacetylphloroglucinol (DAPG)), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12): 5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8):3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, nourseothricin N-acetyl transferase, chloramphenicol, erythromycin, tetracycline, gentamicin, bleomycin, streptomycin, rifampicin, puromycin, hygromycin, blasticidin, and G418 may be employed. In other embodiments, selectable markers include, but are not limited to sugars such as rhamnose. "Selective medium" as used herein refers to cell growth medium to which has been added a chemical compound or biological moiety that selects for or against selectable markers.

The term "specifically binds" as used herein includes an interaction between two molecules, e.g., an engineered peptide antigen and a binding target, with a binding affinity represented by a dissociation constant of about $10^{-7}$ M, about $10^{-8}$ M, about $10^{-9}$ M, about $10^{-10}$ M, about $10^{-11}$ M, about $10^{-12}$ M, about $10^{-13}$ M, about $10^{-14}$ M or about $10^{-15}$ M.

The terms "target genomic DNA sequence", "cellular target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The cellular target sequence can be a genomic locus or extrachromosomal locus.

The term "variant" may refer to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector also comprises in E. coli, the λ Red recombineering system or an equivalent thereto which repairs the double-stranded breaks resulting from the cut by the nuclease. Engine vectors also typically comprise a selectable marker. As used herein the phrase "editing vector" comprises a donor nucleic acid, optionally including an alteration to the cellular target sequence that prevents nuclease binding at a PAM or spacer in the cellular target sequence after editing has taken place, and a coding sequence for a gRNA. The editing vector may also and preferably does comprise a selectable marker and/or a barcode. In some embodiments, the engine vector and editing vector may be combined; that is, all editing and selection components may be found on a single vector. Further, the engine and editing vectors comprise control sequences operably linked to, e.g., the nuclease coding sequence, recombineering system coding sequences (if present), donor nucleic acid, guide nucleic acid(s), and selectable marker(s).

Library Design Strategy and Nuclease-Directed Genome Editing

Figure 1B:
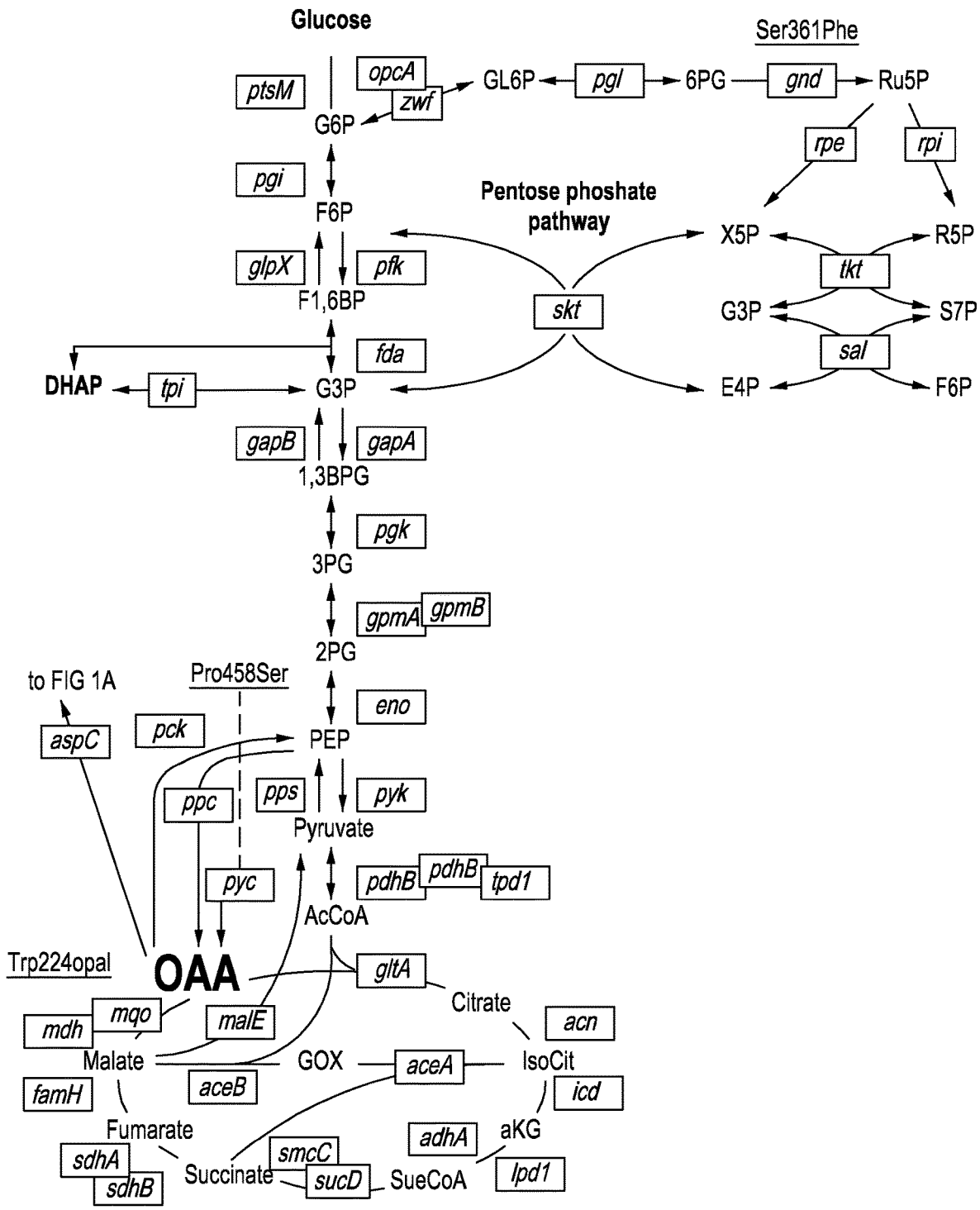

Lysine is naturally synthesized in E. coli along the diaminopimelate (DAP) biosynthetic pathway. See, e.g., FIG. 1. Strain engineering strategies for increasing lysine production in E. coli and other industrially-relevant production hosts such as Corynebacterium glutamicum have historically focused on the genes in the DAP pathway as obvious targets for mutagenesis and over-expression. Beyond this short list of genes encoding the lysine biosynthetic enzymes, it is likely that additional loci throughout the E. coli genome may also contribute appreciably (if less directly) to improved lysine yields in an industrial production setting. For this reason, targeted mutagenesis strategies which enable a broader query of the entire genome are also of significant value to the lysine metabolic engineer.

Figure 3A:
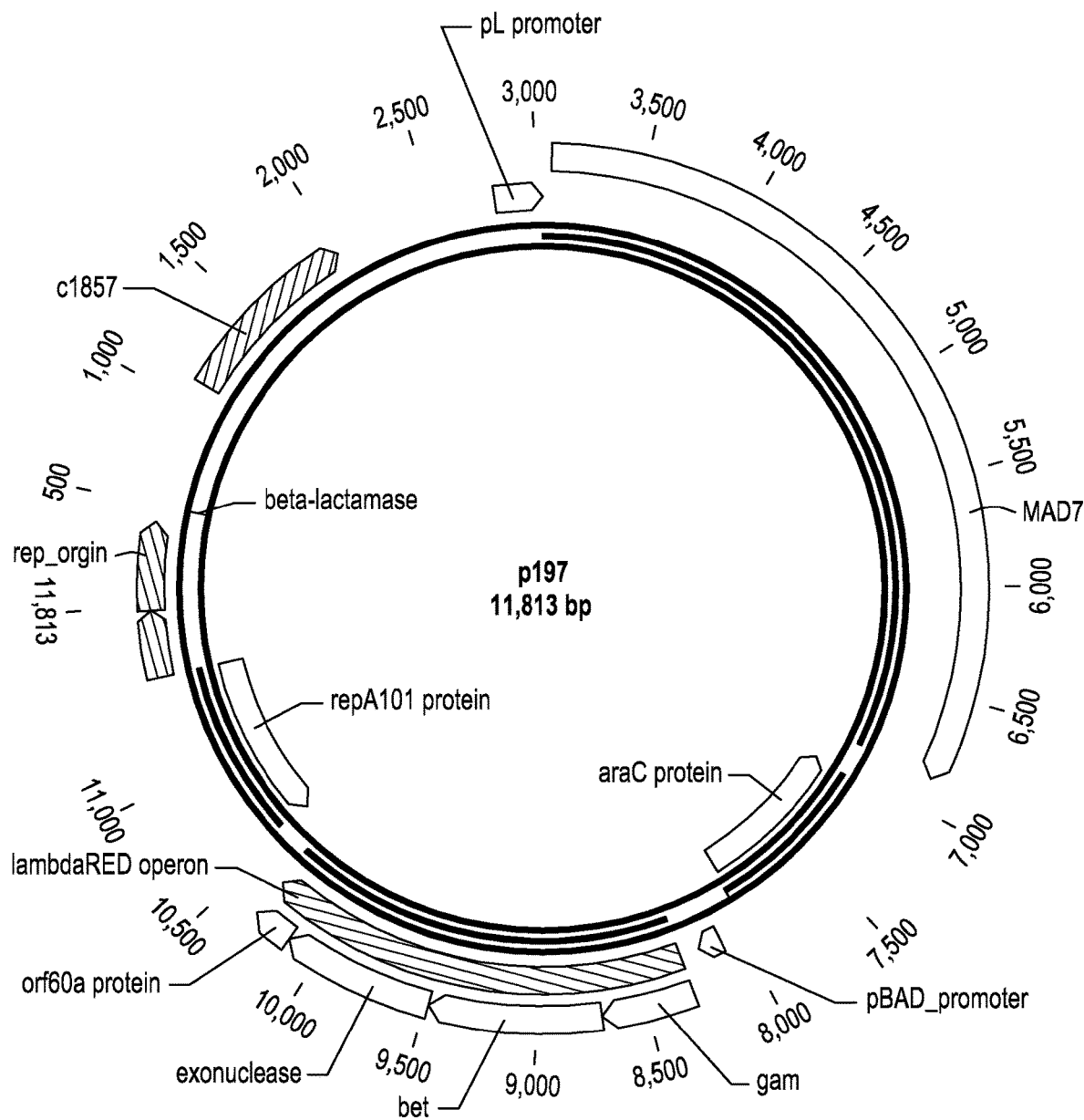
FIG. 3A is an exemplary engine vector for creating edits in *E. coli*.

The variants presented in this disclosure are the result of nucleic acid-guided nuclease editing of 200,000 unique and precise designs at specified loci around the genome in a wildtype strain of E. coli harboring an engine plasmid such as that shown in FIG. 3A (such transformed MG1655 strain is referred to herein as E. coli strain EC83) and using the resulting lysine production levels to conduct additional nucleic acid-guided nuclease editing in two engineered strains of MG1655 to produce double- and triple-variant engineered strains. The first engineered strain is strain MG1655 with a single mutation comprising dapA E84T (SEQ ID No. 1), the lysine production for which was approximately 500-fold over wildtype lysine production in MG1655. The second engineered strain is strain MG1655 with a double mutation comprising dapA E84T (SEQ ID No. 1) and dapA J23100 (a mutation in the E. coli dapA promoter, SEQ ID NO. 2), the lysine production for which was approximately 10,000-fold over wildtype lysine production. See, e.g., FIG. 2 for a summary of the types of edits included in the 200,000 editing vectors used to generate the variants. The engine plasmid comprises a coding sequence for the MAD7 nuclease under the control of the inducible pL promoter, the λ Red operon recombineering system under the control of the inducible pBAD promoter (inducible by the addition of arabinose in the cell growth medium), the c1857 gene under the control of a constitutive promoter, as well as a selection marker and an origin of replication. As described above, the λ Red recombineering system repairs the double-stranded breaks resulting from the cut by the MAD7 nuclease. The c1857 gene at 30° C. actively represses the pL promoter (which drives the expression of the MAD7 nuclease and the editing or CREATE cassette on the editing cassette such as the exemplary editing vector shown in FIG. 3B); however, at 42° C., the c1857 repressor gene unfolds or degrades, and in this state the c1857 repressor protein can no longer repress the pL promoter leading to active transcription of the coding sequence for the MAD7 nuclease and the editing (e.g., CREATE) cassette.

Figure 3B:
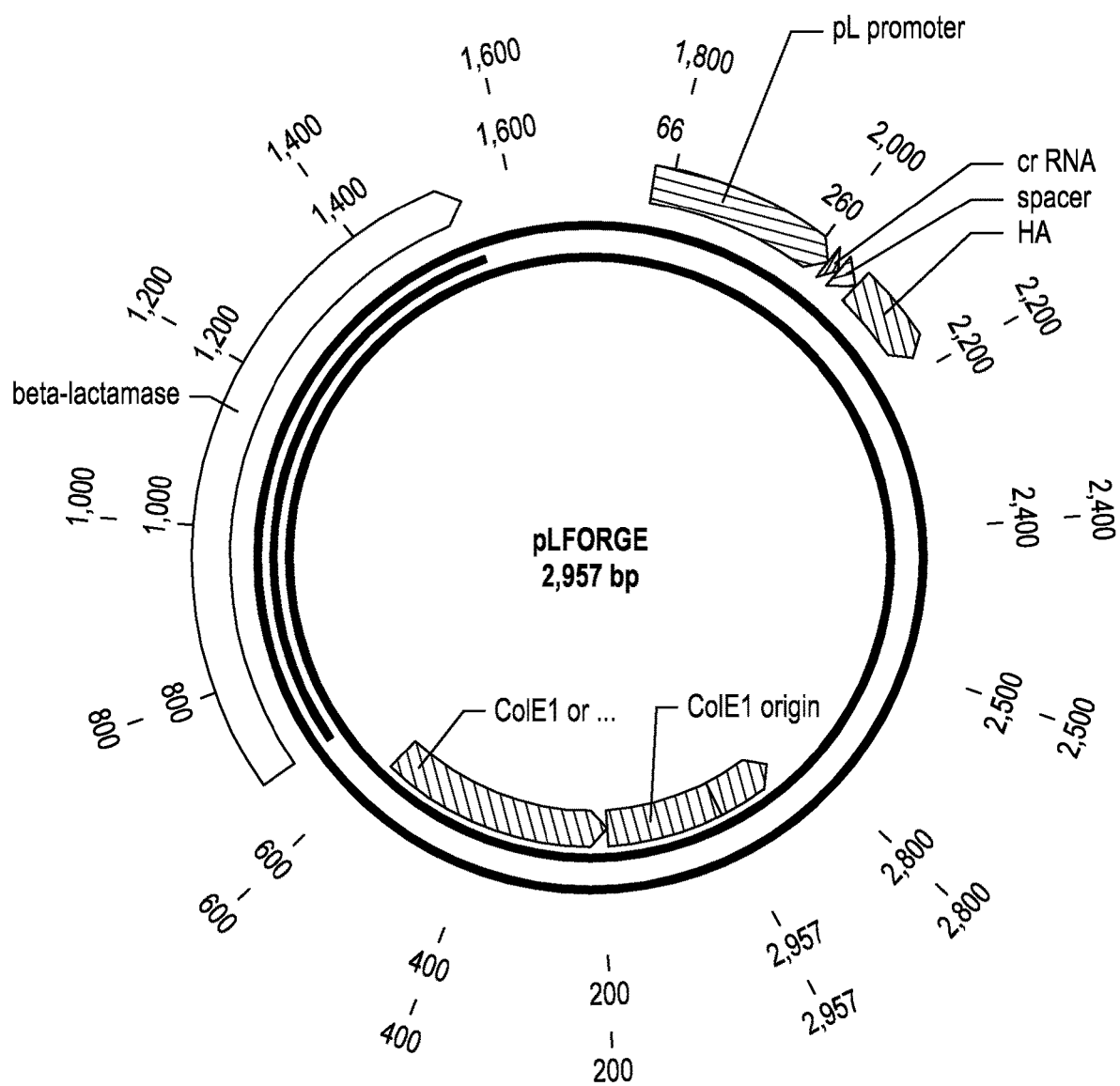
FIG. 3B is an exemplary editing vector for creating edits in *E. coli*.

FIG. 3B depicts an exemplary editing plasmid comprising the editing (e.g, CREATE) cassette (crRNA, spacer and HA) driven by a pL promoter, a selection marker, and an origin of replication.

Mutagenesis libraries specifically targeting the genes in the DAP pathway—along with a number of genes whose enzymes convert products feeding into the DAP pathway—were designed for saturation mutagenesis. Additionally, to more deeply explore the rest of the genome for new targets involved in lysine biosynthesis, libraries were designed to target all annotated loci with either premature stop codons (for a knock-out phenotype) or insertion of a set of five synthetic promoter variants (for expression modulation phenotypes).

The 200,000 nucleic acid mutations or edits described herein were generated using MAD7, along with a gRNA and donor DNA. A nucleic acid-guided nuclease such as MAD7 is complexed with an appropriate synthetic guide nucleic acid in a cell and can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby. In certain aspects, the nucleic acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects, the guide nucleic acid may be a single guide nucleic acid that includes both the crRNA and tracrRNA sequences.

Again, the resulting lysine production levels from the single variants were used to conduct additional nucleic acid-guided nuclease editing in two engineered strains of MG1655 to produce double- and triple-variant engineered strains. The first engineered strain is strain MG1655 with a single mutation comprising dapA E84T (SEQ ID No. 1), the lysine production for which was approximately 500-fold over wildtype lysine production in MG1655. The second engineered strain is strain MG1655 with a double mutation comprising dapA E84T (SEQ ID No. 1) and dapA J23100 (a mutation in the E. coli dapA promoter, SEQ ID NO. 2), the lysine production for which was approximately 10,000-fold over wildtype lysine production.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the methods to generate the 200,000 member library, the guide nucleic acids were provided as a sequence to be expressed from a plasmid or vector comprising both the guide sequence and the scaffold sequence as a single transcript under the control of an inducible promoter. The guide nucleic acids are engineered to target a desired target sequence by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a protospacer adjacent motif (PAM) sequence adjacent to the target sequence. The target sequences for the genome-wide mutagenesis here encompassed 200,000 unique and precise designs at specified loci around the genome throughout the E. coli genome.

The guide nucleic acid may be and in the processes generating the variants reported herein were part of an editing cassette that also encoded the donor nucleic acid. The target sequences are associated with a proto-spacer mutation (PAM), which is a short nucleotide sequence recognized by the gRNA/nuclease complex. The precise preferred PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence.

In certain embodiments, the genome editing of a cellular target sequence both introduces the desired DNA change to the cellular target sequence and removes, mutates, or renders inactive a proto-spacer mutation (PAM) region in the cellular target sequence. Rendering the PAM at the cellular target sequence inactive precludes additional editing of the cell genome at that cellular target sequence, e.g., upon subsequent exposure to a nucleic acid-guided nuclease complexed with a synthetic guide nucleic acid in later rounds of editing. Thus, cells having the desired cellular target sequence edit and an altered PAM can be selected for by using a nucleic acid-guided nuclease complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM alteration will not be cut, as these edited cells no longer contain the necessary PAM site and will continue to grow and propagate.

As for the nuclease component of the nucleic acid-guided nuclease editing system, a polynucleotide sequence encoding the nucleic acid-guided nuclease can be codon optimized for expression in particular cell types, such as archaeal, prokaryotic or eukaryotic cells. The choice of nucleic acid-guided nuclease to be employed depends on many factors, such as what type of edit is to be made in the target sequence and whether an appropriate PAM is located close to the desired target sequence. Nucleases of use in the methods described herein include but are not limited to Cas 9, Cas 12/Cpf1, MAD2, or MAD7 or other MADzymes. As with the guide nucleic acid, the nuclease is encoded by a DNA sequence on a vector (e.g., the engine vector—see FIG. 3A) and be under the control of an inducible promoter. In some embodiments—such as in the methods described herein—the inducible promoter may be separate from but the same as the inducible promoter controlling transcription of the guide nucleic acid; that is, a separate inducible promoter drives the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

Another component of the nucleic acid-guided nuclease system is the donor nucleic acid comprising homology to the cellular target sequence. In some embodiments, the donor nucleic acid is on the same polynucleotide (e.g., editing vector or editing cassette) as the guide nucleic acid. The donor nucleic acid is designed to serve as a template for homologous recombination with a cellular target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the cellular target sequence (e.g., a homology arm). When optimally aligned, the donor nucleic acid overlaps with (is complementary to) the cellular target sequence by, e.g., about 20, 25, 30, 35, 40, 50, 60, 70, 80, 90 or more nucleotides. In many embodiments, the donor nucleic acid comprises two homology arms (regions complementary to the cellular target sequence) flanking the mutation or difference between the donor nucleic acid and the cellular target sequence. The donor nucleic acid comprises at least one mutation or alteration compared to the cellular target sequence, such as an insertion, deletion, modification, or any combination thereof compared to the cellular target sequence. Various types of edits were introduced herein, including site-directed mutagenesis, saturation mutagenesis, promoter swaps and ladders, knock-in and knock-out edits, SNP or short tandem repeat swaps, and start/stop codon exchanges.

In addition to the donor nucleic acid, an editing cassette may comprise one or more primer sites. The primer sites can be used to amplify the editing cassette by using oligonucleotide primers; for example, if the primer sites flank one or more of the other components of the editing cassette. In addition, the editing cassette may comprise a barcode. A barcode is a unique DNA sequence that corresponds to the donor DNA sequence such that the barcode can identify the edit made to the corresponding cellular target sequence. The barcode typically comprises four or more nucleotides. In some embodiments, the editing cassettes comprise a collection or library gRNAs and of donor nucleic acids representing, e.g., gene-wide or genome-wide libraries of gRNAs and donor nucleic acids. The library of editing cassettes is cloned into vector backbones where, e.g., each different donor nucleic acid is associated with a different barcode.

Variants of interest include those listed in Table 1 below:

TABLE 1

| | Variants | | | |
|---|---|---|---|---|
| SEQ ID No. | Mutant | NCBI Gene ID | Phenotype FOWT | Phenotype FIOPC |
| SEQ ID No. 1* | Single edit: dapA E84T | 946952 | 500 | 0 |
| SEQ ID No. 2** | Single edit: dapA J21300 | 946952 | 1000 | 2 |
| SEQ ID No. 3* | Triple edit: dapA E84T/J21300 + lysC V339P | 946952 + 948531 | 13,500 | 27 |
| SEQ ID No. 4** | Triple edit: dapA E84T/J21300 + garD J23101 | 946952 + 947641 | 13,000 | 26 |
| SEQ ID No. 5** | Triple edit: dapA E84T/J21300 + yicL J23100 | 946952 + 948176 | 13,400 | 26.8 |
| SEQ ID No. 6* | Triple edit: dapA E84T/J21300 + lysP R15*** | 946952 + 946667 | 14,600 | 29.2 |
| SEQ ID No. 7** | Triple edit: dapA E84T/J21300 + mgSA J23100 | 946952 + 945574 | 13,300 | 26.6 |
| SEQ ID No. 8* | Triple edit: dapA E84T/J21300 + pckE100Q | 946952 + 945667 | 13,400 | 26.8 |
| SEQ ID No. 9** | Double edit: dapA J21300 + amyA J23100 | 946952 + 946434 | 804.620 | 1.609 |
| SEQ ID No. 10* | Double edit: dapA J21300 + amyA P15*** | 946952 + 946434 | 784.779 | 1.570 |
| SEQ ID No. 11* | Double edit: dapA J21300 + cysN L5*** | 946952 + 947219 | 1320.758 | 2.642 |
| SEQ ID No. 12** | Double edit: dapA J21300 + dosP J23100 | 946952 + 945815 | 1067.701 | 2.135 |
| SEQ ID No. 13** | Double edit: dapA J21300 + emrE J23100 | 946952 + NA | 1016.806 | 2.034 |
| SEQ ID No. 14** | Double edit: dapA J21300 + focB J23100 | 946952 + 949032 | 913.339 | 1.827 |
| SEQ ID No. 15** | Double edit: dapA J21300 + glnD J23100 | 946952 + 944863 | 1397.503 | 2.795 |
| SEQ ID No. 16* | Double edit: dapA J21300 + glnE V15*** | 946952 + 947552 | 1085.446 | 2.171 |
| SEQ ID No. 17** | Double edit: dapA J21300 + hicB J23100 | 946952 + 946001 | 758.057 | 1.516 |
| SEQ ID No. 18** | Double edit: dapA J21300 + maeB J23100 | 946952 + 946947 | 946.484 | 1.893 |
| SEQ ID No. 19* | Double edit: dapA J21300 + marA Y107D | 946952 + 947613 | 798.469 | 1.597 |
| SEQ ID No. 20* | Double edit: dapA J21300 + metL R241E | 946952 + 948433 | 726.648 | 1.453 |

TABLE 1-continued

Variants

| SEQ ID No. | Mutant | NCBI Gene ID | Phenotype FOWT | Phenotype FIOPC |
|---|---|---|---|---|
| SEQ ID No. 21* | Double edit: dapA J21300 + mfd Y5*** | 946952 + 945681 | 983.267 | 1.967 |
| SEQ ID No. 22* | Double edit: dapA J21300 + nupX R5*** | 946952 + 946655 | 884.027 | 1.768 |
| SEQ ID No. 23* | Double edit: dapA J21300 + pck H232G | 946952 + 945667 | 1409.458 | 2.819 |
| SEQ ID No. 24** | Double edit: dapA J21300 + phoB J23100 | 946952 + 945046 | 781.383 | 1.563 |
| SEQ ID No. 25** | Double edit: dapA J21300 + purM J23100 | 946952 + 946975 | 1633.414 | 3.267 |
| SEQ ID No. 26* | Double edit: dapA J21300 + rlmL F5*** | 946952 + NA | 834.477 | 1.669 |
| SEQ ID No. 27* | Double edit: dapA J21300 + wzxB K5*** | 946952 + 946557 | 793.985 | 1.588 |
| SEQ ID No. 28** | Double edit: dapA J21300 + ydgI J23100 | 946952 + 946148 | 1554.101 | 3.108 |
| SEQ ID No. 29** | Double edit: dapA J21300 + ydjE J23100 | 946952 + 946274 | 778.514 | 1.557 |
| SEQ ID No. 30** | Double edit: dapA J21300 + yicL J23100 | 946952 + 948176 | 854.283 | 1.709 |
| SEQ ID No. 31** | Double edit: dapA J21300 + yliE J23100 | 946952 + 945462 | 979.740 | 1.959 |
| SEQ ID No. 32** | Double edit: dapA J21300 + yohF J23100 | 946952 + 949126 | 858.181 | 1.716 |
| SEQ ID No. 33* | Double edit: dapA J21300 + ytfP N15*** | 946952 + 948741 | 781.981 | 1.564 |
| SEQ ID No. 34* | Double edit: dapA J21300 + marA R94* | 946952 + 947613 | 728.433 | 1.457 |
| SEQ ID No. 35* | Double edit: dapA J21300 + marA Y107K | 946952 + 947613 | 733.943 | 1.468 |
| SEQ ID No. 36* | Double edit: dapA J21300 + metL P240D | 946952 + 948433 | 726.648 | 1.453 |
| SEQ ID No. 37* | Double edit: dapA J21300 + metL V235C | 946952 + 948433 | 708.124 | 1.416 |
| SEQ ID No. 38* | Double edit: dapA J21300 + pck G64D | 946952 + 945667 | 718.020 | 1.436 |
| SEQ ID No. 39** | Double edit: dapA J21300 + setB J23100 | 946952 + 946673 | 727.174 | 1.454 |
| SEQ ID No. 40** | Double edit: dapA J21300 + ydfO J23100 | 946952 + 945992 | 701.255 | 1.403 |
| SEQ ID No. 41** | Double edit: dapA J21300 + ydgD J23100 | 946952 + 946436 | 716.198 | 1.432 |
| SEQ ID No. 42** | Double edit: dapA J21300 + yejG J23100 | 946952 + 945319 | 731.562 | 1.463 |

In the table, *denotes an amino acid sequence (e.g., a change to the coding region of the protein), denotes a nucleic acid sequence (e.g., a change to the promoter region or other noncoding region of the protein), "NCBI-GeneID" is the NCBI accession number, "Phenotype FOWT" is fold over wild type (MG1655) in minimal medium; "Phenotype FIOPC" is fold improved over positive control which is MG1655 with E84T single variant. J231XX is a promoter swap at a given locus, and **denotes for hits from the genome-wide knock out library where a triple-stop was inserted at a given position in the locus. Note that the fold over wildtype was equal to or greater than 13,000-fold for all triple edits (SEQ ID Nos. 3-8) and as high as 1600-fold in the double mutant dapA J21300 + purM J23100 (SEQ ID No. 25).

EXAMPLES

Mutagenesis libraries specifically targeting the genes the DAP pathway, along with a number of genes whose enzymes convert products feeding into the DAP pathway were designed for saturation mutagenesis. Additionally, to more deeply explore the rest of the E. coli genome for new targets involved in lysine biosynthesis, libraries were designed to target all annotated loci with either premature stop codons (for a knock-out phenotype) or with an insertion of a set of five synthetic promoter variants (for expression modulation phenotypes). Then, the resulting lysine production levels from the single variants were used to conduct additional nucleic acid-guided nuclease editing in two engineered strains of MG1655 to produce double- and triple-variant engineered strains. The first engineered strain is strain MG1655 with a single mutation comprising dapA E84T (SEQ ID No. 1), the lysine production for which was approximately 500-fold over wildtype lysine production in MG1655. The second engineered strain is strain MG1655 with a double mutation comprising dapA E84T (SEQ ID No. 1) and dapA J23100 (a mutation in the E. coli dapA promoter, SEQ ID NO. 2), the lysine production for which was approximately 10,000-fold over wildtype lysine production. All libraries were screened at shallow sampling for lysine production via mass spec as described below.

Editing Cassette and Backbone Amplification and Assembly

Editing Cassette Preparation: 5 nM oligonucleotides synthesized on a chip were amplified using Q5 polymerase in 50 μL volumes. The PCR conditions were 95° C. for 1 minute; 8 rounds of 95° C. for 30 seconds/60° C. for 30 seconds/72° C. for 2.5 minutes; with a final hold at 72° C. for 5 minutes. Following amplification, the PCR products were subjected to SPRI cleanup, where 30 μL SPRI mix was added to the 50 μL PCR reactions and incubated for 2 minutes. The tubes were subjected to a magnetic field for 2 minutes, the liquid was removed, and the beads were washed 2× with 80% ethanol, allowing 1 minute between washes. After the final wash, the beads were allowed to dry for 2 minutes, 50 µL 0.5× TE pH 8.0 was added to the tubes, and the beads were vortexed to mix. The slurry was incubated at room temperature for 2 minutes, then subjected to the magnetic field for 2 minutes. The eluate was removed and the DNA quantified.

Following quantification, a second amplification procedure was carried out using a dilution of the eluate from the SPRI cleanup. PCR was performed under the following conditions: 95° C. for 1 minute; 18 rounds of 95° C. for 30 seconds/72° C. for 2.5 minutes; with a final hold at 72° C. for 5 minutes. Amplicons were checked on a 2% agarose gel and pools with the cleanest output(s) were identified. Amplification products appearing to have heterodimers or chimeras were not used.

Backbone Preparation: A 10-fold serial dilution series of purified backbone was performed, and each of the diluted backbone series was amplified under the following conditions: 95° C. for 1 minute; then 30 rounds of 95° C. for 30 seconds/60° C. for 1.5 minutes/72° C. for 2.5 minutes; with a final hold at 72° C. for 5 minutes. After amplification, the amplified backbone was subjected to SPRI cleanup as described above in relation to the cassettes. The backbone was eluted into 100 µL ddH$_2$O and quantified before nucleic acid assembly.

Isothermal Nucleic Acid Assembly: 150 ng backbone DNA was combined with 100 ng cassette DNA. An equal volume of 2× Gibson Master Mix was added, and the reaction was incubated for 45 minutes at 50° C. After assembly, the assembled backbone and cassettes were subjected to SPRI cleanup, as described above.

Transformation of Editing Vector Library into E cloni®

Transformation: 20 µL of the prepared editing vector Gibson Assembly reaction was added to 30 µL chilled water along with 10 µL E cloni® (Lucigen, Middleton, Wis.) supreme competent cells. An aliquot of the transformed cells were spot plated to check the transformation efficiency, where >100× coverage was required to continue. The transformed E cloni® cells were outgrown in 25 mL SOB+100 µg/mL carbenicillin (carb). Glycerol stocks were generated from the saturated culture by adding 500 µL 50% glycerol to 1000 µL saturated overnight culture. The stocks were frozen at −80° C. This step is optional, providing a ready stock of the cloned editing library. Alternatively, Gibson or another assembly of the editing cassettes and the vector backbone can be performed before each editing experiment.

Creation of New Cell Line Transformed With Engine Vector:

Transformation: 1 µL of the engine vector DNA (comprising a coding sequence for MAD7 nuclease under the control of the pL inducible promoter, a chloramphenicol resistance gene, and the λ Red recombineering system) was added to 50 µL EC83 strain *E. coli* cells. The transformed cells were plated on LB plates with 25 µg/mL chloramphenicol (chlor) and incubated overnight to accumulate clonal isolates. The next day, a colony was picked, grown overnight in LB+25 µg/mL chlor, and glycerol stocks were prepared from the saturated overnight culture by adding 500 µL 50% glycerol to 1000 µL culture. The stocks of EC1 comprising the engine vector were frozen at −80° C.

Preparation of Competent Cells:

A 1 mL aliquot of a freshly-grown overnight culture of EC83 cells transformed with the engine vector was added to a 250 mL flask containing 100 mL LB/SOB+25 µg/mL chlor medium. The cells were grown to 0.4-0.7 OD, and cell growth was halted by transferring the culture to ice for 10 minutes. The cells were pelleted at 8000×g in a JA-18 rotor for 5 minutes, washed 3× with 50 mL ice cold ddH$_2$O or 10% glycerol, and pelleted at 8000×g in JA-18 rotor for 5 minutes. The washed cells were resuspended in 5 mL ice cold 10% glycerol and aliquoted into 200 µL portions. Optionally at this point the glycerol stocks could be stored at −80° C. for later use.

Screening of Edited Libraries for Lysine Production:

Library stocks were diluted and plated onto 245×245 mm LB agar plates (Teknova) containing 100 µg/mL carbenicillin (Teknova) and 25 µg/mL chloramphenicol (Teknova) using sterile glass beads. Libraries were diluted an appropriate amount to yield ~2000-3000 colonies on the plates. Plates were incubated ~16 h at 30° C. and then stored at 4° C. until use. Colonies were picked using a QPix™ 420 (Molecular Devices) and deposited into sterile 1.2 mL square 96-well plates (Thomas Scientific) containing 300 µL of overnight growth medium (EZ Rich Defined Medium, w/o lysine (Teknova), 100 µg/mL carbenicillin and 25 µg/mL chloramphenicol). Plates were sealed (AirPore sheets (Qiagen)) and incubated for ~19 h in a shaker incubator (Climo-Shaker ISF1-X (Kuhner), 30° C., 85% humidity, 250 rpm). Plate cultures were then diluted 20-fold (15 µL culture into 285 µL medium) into new 96-well plates containing lysine production medium (20 g/L ammonium sulfate (Teknova), 200 mM MOPS buffer (Teknova), 3 mg/L Iron (II) sulfate heptahydrate (Sigma), 3 mg/L Manganese (II) sulfate monohydrate (Sigma), 0.5 mg/L Biotin (Sigma), 1 mg/L Thiamine hydrochloride (Sigma), 0.7 g/L Potassium chloride (Teknova), 20 g/L glucose (Teknova), 5 g/L Potassium phosphate monobasic (Sigma), 1 mL/L Trace metal mixture (Teknova), 1 mM Magnesium sulfate (Teknova), 100 µg/mL carbenicillin and 25 µg/mL chloramphenicol). Production plates were incubated for 24 h in a shaker incubator (Climo-Shaker ISF1-X (Kuhner), 30° C., 85% humidity, 250 rpm).

Production plates were centrifuged (Centrifuge 5920R, Eppendorf) at 3,000 g for 10 min to pellet cells. The supernatants from production plates were diluted 100-fold into water (5 µL of supernatant with 495 µL) of water in 1.2 mL square 96-well plates. Samples were thoroughly mixed and then diluted a subsequent 10-fold further into a 50:50 mixture of acetonitrile and water (20 µL sample with 180 µL of the acetonitrile/water mixture) into a 96-well Plate (polypropylene, 335 µL/well, Conical Bottom (Thomas Scientific). Plates were heat sealed and thoroughly mixed.

Lysine concentrations were determined using a RapidFire high-throughput mass spectrometry system (Agilent) coupled to a 6470 Triple Quad mass spectrometer (Agilent). The RapidFire conditions were as follows: Pump 1: 80% acetonitrile (LC/MS grade, Fisher), 20% water (LC/MS grade, Fisher), 1.5 mL/min, Pump 2: 100% water, 1.25 mL/min, Pump 3: 5% acetonitrile, 95% water, 1.25 mL/min. RapidFire method: Aspirate: 600 ms, Load/wash: 2000 ms, Extra wash: 0 ms, Elute: 3000 ms, Re-equilibrate: 500 ms. 10 µL injection loop.

Mass Spectrometry Conditions for Lysine Detection:

Precursor ion: 147.1 m/z, Product ion (quantifying): 84 m/z, Dwell: 20, Fragmentor: 80, Collision energy: 20, Cell accelerator voltage: 4, Polarity: positive Precursor ion: 147.1 m/z, Product ion (qualifying): 130 m/z, Dwell: 20, Fragmentor: 80, Collision energy: 8, Cell accelerator voltage: 4, Polarity: positive Source conditions: Gas Temp: 300° C., Gas Flow: 10 L/min, Nebulizer: 45 psi, Sheath gas temp: 350° C., Sheath gas flow: 11 L/min, Capillary voltage: 3000V (positive), Nozzle voltage: 1500V (positive)

Data was analyzed using MassHunter Quantitative Analysis software (Agilent) with a standard curve of lysine used for quantitation of lysine in the samples. Each 96-well plate of samples contained 4 replicates of the wildtype strain and 4 replicates of the dapA E84T positive control strain to calculate the relative lysine yield of samples compared to the controls. Hits from the primary screen were re-tested in quadruplicate using a similar protocol as described above.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. An engineered *E. coli* cell comprising the following variant sequences: a promoter sequence having the nucleic acid SEQ ID NO: 2 driving transcription of a dapA gene, and further comprising one of the following proteins expression of which is not driven by a promoter sequence having a nucleic acid of SEQ ID NO: 2: a mfdY5 protein having the amino acid sequence of SEQ ID NO: 21, a nupXR5 protein having the amino acid sequence of SEQ ID NO: 22, a pck protein having the amino acid sequence of SEQ ID NO: 23, a rlmL protein having the amino acid sequence of SEQ ID NO: 26, a wzxB protein having the amino acid sequence of SEQ ID NO: 27, a ytfP protein having the amino acid sequence of SEQ ID NO: 33, a marA protein having the amino acid sequence of SEQ ID NO: 34, a marA protein having the amino acid sequence of SEQ ID NO: 35, a metL protein having the amino acid sequence of SEQ ID NO: 36, a metL protein having the amino acid sequence of SEQ ID NO: 37, a pck protein having the amino acid sequence of SEQ ID NO: 38.

2. The engineered *E. coli* cell of claim 1 comprising the promoter sequence having the nucleic acid SEQ ID NO: 2 driving transcription of the dapA gene and further comprising the mfdY5 protein having the amino acid sequence of SEQ ID NO: 21.

3. The engineered *E. coli* cell of claim 1 comprising the promoter sequence having the nucleic acid SEQ ID NO: 2 driving transcription of the dapA gene and further comprising the nupXR5 protein having the amino acid sequence of SEQ ID NO: 22.

4. The engineered *E. coli* cell of claim 1 comprising the promoter sequence having the nucleic acid SEQ ID NO: 2 driving transcription of the dapA gene and further comprising the pck protein having the amino acid sequence of SEQ ID NO: 23.

5. The engineered *E. coli* cell of claim 1 comprising the promoter sequence having the nucleic acid SEQ ID NO: 2 driving transcription of the dapA gene and further comprising the rlmL protein having the amino acid sequence of SEQ ID NO: 26.

6. The engineered *E. coli* cell of claim 1 comprising the promoter sequence having the nucleic acid SEQ ID NO: 2 driving transcription of the dapA gene and further comprising the wzxB protein having the amino acid sequence of SEQ ID NO: 27.

7. The engineered *E. coli* cell of claim 1 comprising the promoter sequence having the nucleic acid SEQ ID NO: 2 driving transcription of the dapA gene and further comprising the ytfP protein having the amino acid sequence of SEQ ID NO: 33.

8. The engineered *E. coli* cell of claim 1 comprising the promoter sequence having the nucleic acid SEQ ID NO: 2 driving transcription of the dapA gene and further comprising the marA protein having the amino acid sequence of SEQ ID NO: 34.

9. The engineered *E. coli* cell of claim 1 comprising the promoter sequence having the nucleic acid SEQ ID NO: 2 driving transcription of the dapA gene and further comprising the marA protein having the amino acid sequence of SEQ ID NO: 35.

10. The engineered *E. coli* cell of claim 1 comprising the promoter sequence having the nucleic acid SEQ ID NO: 2 driving transcription of the dapA gene and further comprising the metL protein having the amino acid sequence of SEQ ID NO: 36.

11. The engineered *E. coli* cell of claim 1 comprising the promoter sequence having the nucleic acid SEQ ID NO: 2 driving transcription of the dapA gene and further comprising the metL protein having the amino acid sequence of SEQ ID NO: 37.

12. The engineered *E. coli* cell of claim 1 comprising the promoter sequence having the nucleic acid SEQ ID NO: 2 driving transcription of the dapA gene and further comprising the pck protein having the amino acid sequence of SEQ ID NO: 38.

13. An engineered *E. coli* cell comprising the following variant sequences: a promoter sequence having the nucleic acid SEQ ID NO: 2 driving transcription of a dapA gene, and further comprising one of the following: a promoter sequence having the nucleic acid sequence of SEQ ID NO: 24 driving expression of a phoB protein; a promoter sequence having the nucleic acid sequence of SEQ ID NO: 25 driving expression of a purM protein; a promoter sequence having the nucleic acid sequence of SEQ ID NO: 28 driving expression of a ydgl protein; a promoter sequence having the nucleic acid sequence of SEQ ID NO: 29 driving expression of a ydgE protein; a promoter sequence having the nucleic acid sequence of SEQ ID NO: 30 driving expression of a yicL protein; a promoter sequence having the nucleic acid sequence of SEQ ID NO: 31 driving of a yliE protein; a promoter sequence having the nucleic acid sequence of SEQ ID NO: 32 driving expression of a yohF protein; a promoter sequence having the nucleic acid sequence of SEQ ID NO: 39 driving expression of a setB protein; a promoter sequence having the nucleic acid sequence of SEQ ID NO: 40 driving expression of a ydfO protein; a promoter sequence having the nucleic acid sequence of SEQ ID NO: 41 driving expression of a ydgD protein; or a promoter sequence having the nucleic acid sequence of SEQ ID NO: 42 driving expression of a yejD protein.

14. The engineered *E. coli* cell of claim 13 comprising the promoter sequence having the nucleic acid SEQ ID NO: 2 driving transcription of the dapA gene and further comprising the promoter sequence having the nucleic acid sequence of SEQ ID NO: 24 driving expression of the phoB protein.

15. The engineered *E. coli* cell of claim 13 comprising the promoter sequence having the nucleic acid SEQ ID NO: 2 driving transcription of the dapA gene and further comprising the promoter sequence having the nucleic acid sequence of SEQ ID NO: 25 driving expression of the purM protein.

16. The engineered *E. coli* cell of claim 13 comprising the promoter sequence having the nucleic acid SEQ ID NO: 2 driving transcription of the dapA gene and further comprising the promoter sequence having the nucleic acid sequence of SEQ ID NO: 28 driving expression of the ydgl protein.

17. The engineered *E. coli* cell of claim 13 comprising the promoter sequence having the nucleic acid SEQ ID NO: 2 driving transcription of the dapA gene and further comprising the promoter sequence having the nucleic acid sequence of SEQ ID NO: 29 driving expression of the ydgE protein.

18. The engineered *E. coli* cell of claim 13 comprising the promoter sequence having the nucleic acid SEQ ID NO: 2 driving transcription of the dapA gene and further comprising the promoter sequence having the nucleic acid sequence of SEQ ID NO: 30 driving expression of the yicL protein.

19. The engineered *E. coli* cell of claim 13 comprising the promoter sequence having the nucleic acid SEQ ID NO: 2 driving transcription of the dapA gene and further comprising the promoter sequence having the nucleic acid sequence of SEQ ID NO: 31 driving expression of the yliE protein.

20. The engineered *E. coli* cell of claim 13 comprising the promoter sequence having the nucleic acid SEQ ID NO: 2 driving transcription of the dapA gene and further comprising the promoter sequence having the nucleic acid sequence of SEQ ID NO: 32 driving expression of the ydgl protein.

21. The engineered *E. coli* cell of claim 13 comprising the promoter sequence having the nucleic acid SEQ ID NO: 2 driving transcription of the dapA gene and further comprising the promoter sequence having the nucleic acid sequence of SEQ ID NO: 39 driving expression of the setB protein.

22. The engineered *E coli* cell of claim 13 comprising the promoter sequence having the nucleic acid SEQ ID NO: 2 driving transcription of the dapA gene and further comprising the promoter sequence having the nucleic acid sequence of SEQ ID NO: 40 driving expression of the ydfO protein.

23. The engineered *E. coli* cell of claim 13 comprising the promoter sequence having the nucleic acid SEQ ID NO: 2 driving transcription of the dapA gene and further comprising the promoter sequence having the nucleic acid sequence of SEQ ID NO: 41 driving expression of the ydgD protein.

24. The engineered *E. coli* cell of claim 13 comprising the promoter sequence having the nucleic acid SEQ ID NO: 2 driving transcription of the dapA gene and further comprising the promoter sequence having the nucleic acid sequence of SEQ ID NO: 43 driving expression of the yejG protein.

* * * * *